US012742146B2

(12) United States Patent
Lewis et al.

(10) Patent No.: US 12,742,146 B2
(45) **Date of Patent: *Sep. 22, 2026**

(54) ***BACILLUS SUBTILIS* SUBSPECIES**

(71) Applicant: Novozymes A/S, Bagsvaerd (DK)

(72) Inventors: Derrick Lewis, Durham, NC (US); Marianne Thorup Cohn, Copenhagen (DK); Adam Nelson, Salem, VA (US); Preben Nielsen, Horsholm (DK); Ravi Kumar, Davis, CA (US)

(73) Assignee: Novozymes A/S, Bagsvaerd (DK)

( * ) Notice: Subject to any disclaimer, the term of this patent is extended or adjusted under 35 U.S.C. 154(b) by 181 days.

This patent is subject to a terminal disclaimer.

(21) Appl. No.: 17/934,003

(22) Filed: Sep. 21, 2022

(65) Prior Publication Data

US 2023/0287329 A1 Sep. 14, 2023

Related U.S. Application Data

(62) Division of application No. 15/542,135, filed as application No. PCT/US2016/014505 on Jan. 22, 2016, now Pat. No. 11,473,052.

(60) Provisional application No. 62/260,800, filed on Nov. 30, 2015, provisional application No. 62/153,038, filed on Apr. 27, 2015, provisional application No. 62/106,841, filed on Jan. 23, 2015.

(51) Int. Cl.

| | |
|---|---|
| ***C12N 1/20*** | (2026.01) |
| ***C12N 1/205*** | (2026.01) |
| *A23K 10/18* | (2016.01) |
| *A61K 35/00* | (2006.01) |
| *A61P 31/04* | (2006.01) |
| *C12R 1/125* | (2006.01) |

(52) U.S. Cl.

CPC ............... *C12N 1/20* (2013.01); *C12N 1/205* (2021.05); *A23K 10/18* (2016.05); *A61K 2035/115* (2013.01); *A61P 31/04* (2018.01); *C12R 2001/125* (2021.05)

(58) Field of Classification Search

CPC ....................................................... C12N 1/20

See application file for complete search history.

(56) References Cited

U.S. PATENT DOCUMENTS

| | | | |
|---|---|---|---|
| 4,919,936 | A | 4/1990 | Iwanami |
| 5,733,355 | A | 3/1998 | Hibino |
| 8,540,981 | B1 | 9/2013 | Wehnes |
| 8,906,668 | B2 | 12/2014 | Henn |
| 11,166,989 | B2 | 11/2021 | Lewis et al. |
| 11,331,351 | B2 | 5/2022 | Lewis et al. |
| 11,473,052 | B2 | 10/2022 | Lewis |
| 12,364,720 | B2 | 7/2025 | Lewis et al. |
| 2004/0101525 | A1 | 5/2004 | In |
| 2009/0280090 | A1 | 11/2009 | Rehberger |
| 2009/0318292 | A1 | 12/2009 | Kong |
| 2011/0318289 | A1 | 12/2011 | Frodyma |
| 2013/0136695 | A1 | 5/2013 | Hargis |
| 2013/0330307 | A1 | 12/2013 | Millan |
| 2014/0037582 | A1 | 2/2014 | Romero |
| 2014/0234279 | A1 | 8/2014 | Millan |
| 2016/0051599 | A1 | 2/2016 | Drahos et al. |
| 2023/0287329 | A1 | 9/2023 | Lewis et al. |
| 2024/0075077 | A1 | 3/2024 | Lewis |

FOREIGN PATENT DOCUMENTS

| | | | |
|---|---|---|---|
| CN | 103882097 | | 6/2014 |
| WO | 2007064741 | A2 | 6/2007 |
| WO | 2010033714 | A1 | 3/2010 |
| WO | 2012009712 | A2 | 1/2012 |
| WO | 2012105805 | A2 | 9/2012 |
| WO | 2013029013 | A1 | 2/2013 |
| WO | 2013096369 | A1 | 6/2013 |
| WO | 2013153159 | A1 | 10/2013 |
| WO | 2014151837 | A1 | 9/2014 |
| WO | 2014169046 | A1 | 10/2014 |
| WO | 2016118864 | A1 | 7/2016 |

OTHER PUBLICATIONS

Bampidis et al., EFSA Journal, 2022, 7244, 20(4).
Anonymous, 2023, sequence alignment Appendix B.
Abdollahi et al., 2013, Animal Feed Science and Technology, 179, 1-23.
Annoymous, 2023, Calcium carbonate, Britannica Online Encyclopedia, 1-2.
Anonymous, 2024, Appendix D, sequence alignment of SEQ ID No. 2 and CP025079.
Essghaier et al., 2009, Bacillus subtilis strain B1-33 16S ribosomal RNA gene, partial sequence, Accession No. EU435361.
Källqvist et al., 2016, VKM Report, 1-25, 21.
Lancheros et al., 2020, Animal Feed Science and Technology, 268, 114603.
Pandin et al., 2018, J Biotechnol 278, 10-19.
Ramos et al., 1997, Animal Feed Science and Technology, 65, 197-206.
Rowe(ed) et al., 2009, Handbook of Pharmaceutical Excipients 6th Ed, 185-188.
Sapkota et al., 2007, Environmental Health Perspectives, 115, 5, 663.
Song et al., 2012, Probiotics 10.1, 1-34.
Sueoka, 1997, Progress in Nucleic Acid Research and Molecular Biology 69, 35-53.

(Continued)

*Primary Examiner* — Yong D Pak
(74) *Attorney, Agent, or Firm* — Adam Rucker

(57) ABSTRACT

The present application relates to novel subspecies of *Bacillus*. The novel subspecies can improve health and performance of production animals. In one embodiment the *Bacillus subtilis* subspecies has activity against *Clostridium perfringens* and/or *E. coli*. The present application further relates to compositions comprising one or more strains of the *Bacillus subtilis* subspecies and to use of the strain(s) of the *Bacillus subtilis* subspecies in an animal feed.

18 Claims, 4 Drawing Sheets

Specification includes a Sequence Listing.

(56) References Cited

OTHER PUBLICATIONS

Anonymous,2010 EFSA Journal vol. 8, No. 3 p. 1552.
Anonymous, 2012 EFSA J Animal Feed pp. 1-19.
Anonymous, 2014 Eur Food Safety Authority pp. 1-13.
Essghaier 2009 J Appl Microbiol, vol. 106, No. 3, pp. 833-846.
Gang 2015 Biomed Environ Sci, vol. 28, No. 8, pp. 620-625.
Jayaraman 2013 Poultry Science, vol. 92, No. 2, pp. 370-374.
Knap 2010 Avian Diseases, vol. 54, No. 2, pp. 931-935.
Maruta 1996 Animal Sci Technol, vol. 67, No. 5, pp. 403-409.
Paineau, 2008 FEMS Immuno Med Microbiol vol. 53, pp. 107-113.
Prieto 2014 Marine Drugs, vol. 12, No. 5, pp. 2422-2445.
Sathishkumar, 2013 Kemin-Clostat.
Tactacan 2013 J Applied Poultry Research, vol. 22, No. 4, pp. 825-831.
Teo 2006 Journal Applied Poultry Research, vol. 15, No. 2, pp. 229-235.
Zeigler, 2010 UniprotKB No. E0TXL5 Bacpz.

| Bamy= *Bacillus amyloliquefaciens* | Batr= *B. atrophaeus* | Bsub= *B. subtilis* | Bthu= *B. thuringiensis* |
|---|---|---|---|
| Blic= *B. licheniformis* | Bson= *B. sonorensis* | Bpum= *B. pumilus* | |
| Bmeg= *B. megaterium* | Bcl= *B. clausii* | Bcoa= *B. coagulans* | |
| Bmyc= *B. mycoides* | Banth= *B. anthracis* | Bcer= *B. cereus* | |

| Bamy= *Bacillus amyloliquefaciens* | Batr= *B. atrophaeus* | Bsub= *B. subtilis* | Bthu= *B. thuringiensis* |
|---|---|---|---|
| Blic= *B. licheniformis* | Bson= *B. sonorensis* | Bpum= *B. pumilus* | |
| Bmeg= *B. megaterium* | Bcl= *B. clausii* | Bcoa= *B. coagulans* | |
| Bmyc= *B. mycoides* | Banth= *B. anthracis* | Bcer= *B. cereus* | |

*BACILLUS SUBTILIS* SUBSPECIES

CROSS-REFERENCE TO RELATED APPLICATIONS

This application is a divisional of U.S. patent application Ser. No. 15/542,135, filed Jul. 7, 2017, which is a 35 U.S.C. 371 national application of International Patent Application No. PCT/US2016/014505, filed Jan. 22, 2016, which claims priority under 35 U.S.C. 119 to U.S. Provisional Patent Application No. 62/106,841, filed Jan. 23, 2015; 62/153,038, filed Apr. 27, 2015; and 62/260,800, filed Nov. 30, 2015. The contents of each of the aforementioned applications is hereby fully incorporated herein by reference.

REFERENCE TO DEPOSIT OF BIOLOGICAL MATERIALS

This application contains a reference to a deposit of biological material, which deposit is incorporated herein by reference.

REFERENCE TO A SEQUENCE LISTING

This application contains a Sequence Listing in computer readable form, which is incorporated herein by reference. The name of the file containing the Sequence Listing is SQ.XML, which was created on Jun. 2, 2023 and has 61,386 bytes SEQ ID NO: 1 is the DNA sequence of the gyrB gene from DSM 29870 (obtained as described in Example 3).

SEQ ID NO: 2 is the partial amino acid sequence deduced from the gyrB gene of SEQ ID NO: 1 from DSM 29870.

SEQ ID NO: 3 is the DNA sequence of the rpoB gene from DSM 29870 (obtained as described in Example 4).

SEQ ID NO: 4 is the partial amino acid sequence deduced from the rpoB gene of SEQ ID NO: 3 from DSM 29870.

SEQ ID NO: 5 is the DNA sequence of the gyrA gene (published genome sequence of *Bacillus subtilis* subsp. *Spizizenii* CP002905).

SEQ ID NO: 6 is the partial amino acid sequence deduced from the gyrA gene of SEQ ID NO: 5.

SEQ ID NO: 7 is the DNA sequence of the gyrA gene from DSM 29870.

SEQ ID NO: 8 is the amino acid sequence of gyrA gene product of SEQ ID NO: 7 from DSM 29870.

SEQ ID NO: 9 is the 16S rDNA of DSM 29870.

SEQ ID NO: 10 to SEQ ID NO: 31 are PCR and sequencing primers.

SEQ ID NO: 32 is DNA sequence of GyrB gene from DSM 29870 (obtained from PCR product).

SEQ ID NO: 33 is the partial amino acid sequence deduced from the gyrB gene of SEQ ID NO: 32 from DSM 29870.

SEQ ID NO: 34 is DNA sequence of rpoB gene from DSM 29870 (obtained from PCR product).

SEQ ID NO: 35 is the partial amino acid sequence deduced from the rpoB gene of SEQ ID NO: 34 from DSM 29870.

FIELD OF THE INVENTION

The present application relates to novel subspecies of *Bacillus subtilis*. The novel subspecies can improve health and performance of production animals. In one embodiment the *Bacillus subtilis* subspecies has activity against *Clostridium perfringens* and/or *E. coli*. In a preferred embodiment the *Bacillus subtilis* subspecies has a high compatibility with monensin such as being compatible with at least 2.4 μg/ml monensin as determined in Example 12. The present application further relates to compositions comprising one or more strains of the *Bacillus subtilis* subspecies and to use of the strain(s) of the *Bacillus subtilis* subspecies in an animal feed.

BACKGROUND

*Bacillus* is a genus of Gram-positive, rod-shaped bacteria and a member of the phylum Firmicutes. *Bacillus* species can be obligate aerobes (oxygen reliant), or facultative anaerobes (having the ability to be aerobic or anaerobic). Ubiquitous in nature, *Bacillus* includes both free-living (non-parasitic) and parasitic pathogenic species. Under stressful environmental conditions, the bacteria can produce oval endospores that are not true spores but which the bacteria can reduce themselves to and remain in a dormant state for very long periods.

*Clostridium perfringens* (*C. perfringens*) is a Gram-positive, rod-shaped, anaerobic, spore-forming bacterium of the genus *Clostridium*. Infections due to *C. perfringens* show evidence of tissue necrosis, bacteremia, emphysematous cholecystitis, and gas gangrene, which is also known as clostridial myonecrosis. *C. perfringens* can also result in polymicrobial anaerobic infections. The incidence of *Clostridium perfringens*-associated necrotic enteritis in poultry has increased in countries that stopped using antibiotic growth promoters. Necrotic enteritis is an enterotoxemic disease that results in significant economic losses in the poultry industry.

There is a need for development of tools and strategies for prevention and control of *C. perfringens* in mono-gastric animals such as poultry. Whilst the vaccination of animals has been suggested, there are challenges associated with vaccinating thousands of animals. Thus discovering a solution which could be administered as an additive in an animal feed would be advantageous.

It is an object of the invention to provide solutions which prevents and/or controls *C. perfringens* in poultry by use of an animal feed comprising one or more one or more bacteria with activity against *Clostridium perfringens*.

A challenge of delivering *Bacillus* spp. in feed is the common use of antibiotics as growth promoters in feed. Therefore it is necessary to determine the compatibility of strains with commonly-used feed antibiotics such as monensin in order to identify any potential conflicts with use as a direct fed microbial. The present invention relates in one embodiment to a *Bacillus subtilis* subspecies with high compatibility with monensin.

WO 2010/033714 describes a method for enhancing the health of an animal comprising administering to the animal a composition comprising *Bacillus subtilis* QST713.

U.S. Pat. No. 4,919,936 describes a method for increasing the weight gain in animals comprising feeding an animal a probiotic comprising *Bacillus subtilis* C-3102.

Knap et al. describes that *Bacillus licheniformis* has an effect on necrotic enteritis in broiler chickens (Knap et al., 2010, "*Bacillus licheniformis* Prevents Necrotic Enteritis in Broiler Chickens", *Avian Diseases* 54(2):931-935).

DETAILED DESCRIPTION

Figure 1:
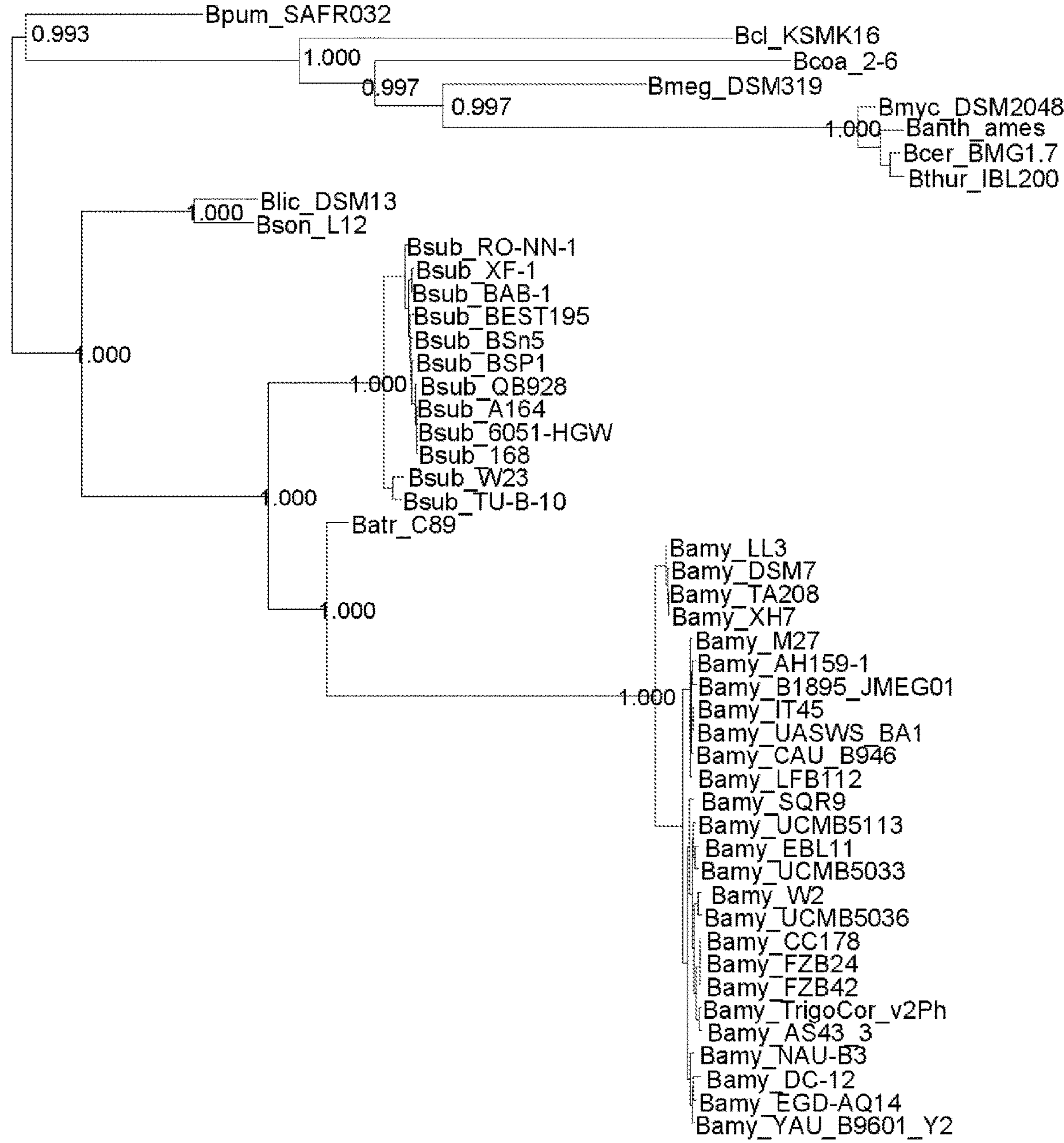
FIG. 1: Core genome phylogram of *Bacillus* species. Note that *B. amyloliquefaciens* subspecies *amyloliquefaciens* and *plantarum* separate with a bootstrap support of 1 (100%).

In general, the terms and phrases used herein have their art-recognized meaning, which can be found by reference to standard texts, journal references, and context known to those skilled in the art. The following definitions are provided to clarify their specific use in context of the disclosure.

As used herein, the singular forms “a”, “an” and “the” are intended to include the plural forms as well, unless the context clearly indicates otherwise.

ANI (Average nuclear identity): DNA-DNA hybridization (DDH) has been used traditionally for phylogenetic definition of a species. Based on DDH, strains with greater than 70% relatedness would be considered to belong to the same species [Wayne et al., 1987, Report of the Ad-Hoc-Committee on Reconciliation of Approaches to Bacterial Systematics. *Int J Syst Bacteriol* 37: 463-464]. With the availability of cheap and affordable whole genome sequencing technologies as well as the increased availability of public genomes, whole genome-based species estimation methods are becoming popular as they offer elegant in silico solutions as alternatives DDH methods. ANI is a distance based approach to delineate species based on pair-wise comparisons of genome sequences [Goris et al., 2007, “DNA-DNA hybridization values and their relationship to whole-genome sequence similarities”, *Int. J. Syst. Evol. Microbiol.* 57: 81-91]. Goris et al. used 28 different strains to conclude that 95% ANI is similar to the aforementioned 70% DDH cutoff value and can be used for species delineation. ANI has been evaluated in multiple labs and has become the gold standard for species delineation [cf. Kim et al., 2014, “Towards a taxonomic coherence between average nucleotide identity and 16S rRNA gene sequence similarity for species demarcation of prokaryotes”, *Int. J. Syst. Evol. Micr.* 64: 346-351; Richter et al., 2009, “Shifting the genomic gold standard for the prokaryotic species definition”, *P Natl Acad Sci USA* 106: 19126-19131; and Chan et al., 2012, “Defining bacterial species in the genomic era: insights from the genus *Acinetobacter”, Bmc. Microbiol.* 12)].

An evaluation of ANI for designation for a strain of *Bacillus amyloliquefaciens* is presented here as an example. ANI calculations were obtained for pair-wise comparisons of *B. amyloliquefaciens* strain FZB42 to members of *B. amyloliquefaciens* subspecies *plantarum, B. amyloliquefaciens* subspecies *amyloliquefaciens, Bacillus atrophaeus* and *Bacillus subtilis*. The ANI calculator on the Kostas lab website (enve-omics.ce.gatech.edu/ani/newjob) was used. Comparisons with *B. subtilis* strain 160 and *B. atrophaeus* strain C89 give ANI less than 90% indicating that ANI can be successfully used to distinguish between these species (Table A).

TABLE A

Pairwise ANI of *B. amyloliquefaciens* FZB42 compared to other bacterial genomes (in percentage).

| | *B. subtilis* | *B. atrophaeus* | *Amyloliquefaciens* subspecies members | | | | *Plantarum* subspecies members | | | |
|---|---|---|---|---|---|---|---|---|---|---|
| | 168 | C89 | DSM7 | LL3 | TA208 | XH7 | AS43_3 | CAU_B946 | EBL11 | YAU_B9601Y2 |
| FZB42 | 83.08 | 82.31 | 94.52 | 94.44 | 94.44 | 94.46 | 99.08 | 97.91 | 99.00 | 98.52 |

FZB42 shows >95% identify with all members of *B. amyloliquefaciens* subspecies *plantarum*, confirming its species designation. However, FZB42 comparisons to DSM7 and other *amyloliquefaciens* subspecies show an ANI of 94-94.5%, which is less than the acceptable species definition cutoff of 95%. Reciprocal comparison of DSM7 to other genomes also shows >95% ANI within the subspecies *amyloliquefaciens* isolates and 94-95% ANI with subspecies *plantarum* isolates (Table B).

TABLE B

Pairwise ANI of *B. amyloliquefaciens* DSM7 compared to other bacterial genomes (in percentage).

| | *B. subtilis* | *B. atrophaeus* | *amyloliquefaciens* subspecies members | | | *plantarum* subspecies members | | | | |
|---|---|---|---|---|---|---|---|---|---|---|
| | 168 | C89 | LL3 | TA208 | XH7 | AS43_3 | CAU_B946 | EBL11 | FZB42 | YAU_B9601Y2 |
| DSM7 | 82.85 | 82.25 | 99.59 | 99.48 | 99.52 | 94.47 | 94.44 | 94.47 | 94.52 | 94.53 |

Borriss et al. also observed that the DDH between FZB42 and DSM7 varied from 63.7-71.2% which are ranges below the DDH threshold of 70% and is one of the many reasons why they were classified into separate subspecies [Borriss et al., 2011, “Relationship of *Bacillus amyloliquefaciens* clades associated with strains DSM 7(T) and FZB42(T): a proposal for *Bacillus amyloliquefaciens* subsp *amyloliquefaciens* subsp nov and *Bacillus amyloliquefaciens* subsp *plantarum* subsp nov based on complete genome sequence comparisons”, *Int. J. Syst. Evol. Micr.* 61: 1786-1801].

Chan et al. recommended complementing ANI with core genome phylogenetics [Chan et al., 2012, “Defining bacterial species in the genomic era: insights from the genus *Acinetobacter”, Bmc. Microbiol.* 12: 302], where common elements (generally coding sequences or their translations) can be used to derive phylogenetic inferences. To test this, Hyatt et al. [Hyatt et al., 2010 "Prodigal: prokaryotic gene recognition and translation initiation site identification", *BMC Bioinformatics* 11: 119] was used for gene calling and PhyloPhlan [Segata et al., 2013, "PhyloPhlAn is a new method for improved phylogenetic and taxonomic placement of microbes", *Nat. Commun.* 4: 2304] was used to generate a core genome phylogenetic tree. Dendroscope 3 [Huson et al., 2012, "Dendroscope 3: an interactive tool for rooted phylogenetic trees and networks", Syst. Biol. 61: 1061-1067] was used to visualize the tree as a rectangular phylogram with midpoint rooting along with bootstrap support (cf. FIG. 1). It is clear that all of the *B. amyloliquefaciens* strains cluster together in one distinct branch; and the *amyloliquefaciens* and *plantarum* subspecies separate into two subclades.

Based on the data presented here, the following species definition could be applied to *B. amyloliquefaciens: "Bacillus amyloliquefaciens*" shall mean a monophyletic group of strains that reside in either *amyloliquefaciens* or *plantarum* subspecies branches of a core genome phylogenetic tree and whose genomes exhibit at least 95% pairwise average-nucleotide identity (ANI) [Goris et al., 2007, "DNA-DNA hybridization values and their relationship to whole-genome sequence similarities", *Int J Syst Evol Microbiol* 57: 81-91] when compared to members of the same subspecies and greater than 94% ANI when compared to members of the other subspecies. Alternative definition: "*Bacillus amyloliquefaciens*" shall mean a monophyletic group of strains whose genomes exhibit at least 95% pairwise average-nucleotide identity (ANI) to type strain DSM7 if belonging to subspecies *amyloliquefaciens* or at least 95% pairwise ANI to type strain FZB42 if belonging to subspecies *plantarum*, as inferred by core genome phylogenetics.

Animal feed: The term "animal feed" refers to any compound, preparation, or mixture suitable for, or intended for intake by an animal. Animal feed for a mono-gastric animal comprises concentrates as well as vitamins, minerals, enzymes, amino acids and/or other feed ingredients (such as in a premix). The animal feed may further comprise forage.

Antimicrobial activity against *Clostridium perfringens*: The term "Antimicrobial activity against *Clostridium perfringens*" means that the growth of *Clostridium perfringens* is inhibited and/or that some or all of the *Clostridium perfringens* are killed. This can be determined by the assay described in Example 6.

Blend: the term "blend" means more than one of the bacterial strains described herein.

Body Weight Gain: The Body Weight Gain of an animal is the increase of body weight of the animal over a specified time period.

Composition: The term "composition" refers to a composition comprising a carrier and at least one bacterial strain as described herein. The compositions described herein may be mixed with an animal feed(s) and referred to as a "mash feed."

Concentrates: The term "concentrates" means feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

Control *C. perfringens* infections and/or necrotic enteritis: The term "control *C. perfringens* infections and/or necrotic enteritis" means a method and/or composition that partly or completely inhibits *C. perfringens* infections and/or necrotic enteritis in an animal. Accordingly, the term "control *C. perfringens* infections and/or necrotic enteritis" means the *C. perfringens* infections and/or the necrotic enteritis is reduced or completely eliminated or prevented.

Direct Fed Microbial: The term "direct fed microbial" means live micro-organisms including spores which, when administered in adequate amounts, confer a benefit, such as improved digestion or health, on the host.

European Production Efficacy Factor (EPEF): The European Production Efficacy Factor is a way of comparing the live-bird performance of flocks. This single-figure facilitates comparison of performance within and among farms and can be used to assess environmental, climatic and managemental variables. The EPEF is calculated as [(liveability (%)× Liveweight (kg))/(Age at depletion (days)×FCR)]×100, wherein livability is the percentage of birds alive at slaughter, Liveweight is the average weight of the birds at slaughter, age of depletion is the age of the birds at slaughter and FCR is the feed conversion ratio at slaughter.

Effective amount/concentration/dosage: The terms "effective amount", "effective concentration", or "effective dosage" are defined as the amount, concentration, or dosage of the bacterial strain(s) sufficient to improve the digestion or yield of an animal or to control *C. perfringens* infections and/or necrotic enteritis. The actual effective dosage in absolute numbers depends on factors including: the state of health of the animal in question, other ingredients present. The "effective amount", "effective concentration", or "effective dosage" of the bacterial strains may be determined by routine assays known to those skilled in the art.

FCR (Feed Conversion Rate): FCR is a measure of an animal's efficiency in converting feed mass into increases of the desired output. Animals raised for meat—such as swine, poultry and fish—the output is the mass gained by the animal. Specifically FCR is the mass of the food eaten divided by the output, all over a specified period.

Feeding an animal: the terms "feeding an animal" or "fed to an animal" means that the composition of the present invention is administered orally to the animal one or more times in an effective amount. The oral administration is typically repeated, e.g., one or more times daily over a specified time period such as several days, one week, several weeks, one months or several months. Accordingly, the term "feeding" or "fed" means any type of oral administration such as administration via an animal feed or via drinking water.

Forage: The term "forage" as defined herein also includes roughage. Forage is fresh plant material such as hay and silage from forage plants, grass and other forage plants, seaweed, sprouted grains and legumes, or any combination thereof. Examples of forage plants are Alfalfa (lucerne), birdsfoot trefoil, brassica (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Isolated: The term "isolated" means that the one or more bacterial strains described herein are in a form or environment which does not occur in nature, that is, the one or more bacterial strains are at least partially removed from one or more or all of the naturally occurring constituents with which it is associated in nature.

Non-hemolytic: Hemolysis is the breakdown of red blood cells. The ability of bacterial colonies to induce hemolysis when grown on blood agar is used to classify bacterial strains into hemolytic and non-hemolytic strains. In this context hemolysis is defined as described in EFSA Journal 2011; 9(11): 2445, using *Bacillus subtilis* 168 (BGSC-1A1, *Bacillus* Genetic Stock Center) as a negative control. A *Bacillus* strain can be classified as non-hemolytic using the assay described in Example 8.

Pellet: The terms "pellet" and/or "pelleting" refer to solid rounded, spherical and/or cylindrical tablets or pellets and the processes for forming such solid shapes, particularly feed pellets and solid extruded animal feed. As used herein, the terms "extrusion" or "extruding" are terms well known in the art and refer to a process of forcing a composition, as described herein, through an orifice under pressure.

Poultry: The term "poultry" means domesticated birds kept by humans for the eggs they produce and/or their meat and/or their feathers. Poultry includes broilers and layers. Poultry include members of the superorder Galloanserae (fowl), especially the order Galliformes (which includes chickens, Guineafowls, quails and turkeys) and the family Anatidae, in order Anseriformes, commonly known as "waterfowl" and including domestic ducks and domestic geese. Poultry also includes other birds that are killed for their meat, such as the young of pigeons. Examples of poultry include chickens (including layers, broilers and chicks), ducks, geese, pigeons, turkeys and quail.

Prevent *C. perfringens* infections and/or necrotic enteritis: The term "prevent *C. perfringens* infections and/or necrotic enteritis" means a method and/or composition that prevents development of a *C. perfringens* infection and/or necrotic enteritis in an animal.

Roughage: The term "roughage" means dry plant material with high levels of fiber, such as fiber, bran, husks from seeds and grains and crop residues (such as stover, copra, straw, chaff, sugar beet waste).

Sensitive to antibiotics: The term "sensitive to antibiotics" means the phenotypic property of a bacterial strain, that growth of said bacterial strain is inhibited under conditions where the bacterial strain would otherwise grow. In this context sensitivity to antibiotics is tested after the CLSI guidelines (M07-A9 Methods for Dilution Antimicrobial Susceptibility Tests for Bacteria That Grow Aerobically; 2012). The *S. aureus* ATCC 29213 is used as reference strain, which means that it should be included in the test, and that the results are only valid if *S. aureus* ATCC 29213 show results in compliance with the breakpoints of the CLSI guideline (see example Table 5.5) (M100-S24 Performance Standards for Antimicrobial Susceptibility Testing; informational Supplement, 2014). A strain of *Bacillus* is considered sensitive if the growth is detected at or below the breakpoint concentration of the appropriate antibiotic specified in EFSA Journal 2012; 10(6): 2740.

Silage: The term "silage" means fermented, high-moisture stored fodder which can be fed to ruminants (cud-chewing animals such as cattle and sheep) or used as a biofuel feedstock for anaerobic digesters. It is fermented and stored in a process called ensilage, ensiling or silaging, and is usually made from grass or cereal crops (e.g., maize, sorghum, oats, rye, timothy etc forage grass plants)) or legume crops like clovers/trefoils, alfalfa, vetches, using the entire green plant (not just the grain). Silage can be made from many field crops, and special terms may be used depending on type (oatlage for oats, haylage for alfalfa). Silage is made either by placing cut green vegetation in a silo, by piling it in a large heap covered with plastic sheet, or by wrapping large bales in plastic film.

Spore: The terms "spore" and "endospore" are interchangeable and have their normal meaning which is well known and understood by those of skill in the art. As used herein, the term spore refers to a microorganism in its dormant, protected state.

Stable: The term "stable" is a term that is known in the art, and in a preferred aspect, stable is intended to mean the ability of the microorganism to remain in a spore form until it is administered to an animal to improve the health of the animal.

Swine: The term "swine" or "pigs" means domesticated pigs kept by humans for food, such as their meat. Swine includes members of the genus *Sus*, such as *Sus scrofa domesticus* or *Sus domesticus* and include piglets, growing pigs, and sows.

Vegetable protein: The term "vegetable protein" refers to any compound, preparation or mixture that includes at least one protein derived from or originating from a vegetable, including modified proteins and protein-derivatives.

It has been surprisingly found that the addition of direct fed microbes (DFM) from *Bacillus* species to animal feed can be used to prevent and/or control *C. perfringens* infections and/or necrotic enteritis in mono-gastric animal such as pigs and/or poultry and at the same time improve the body weight gain and/or feed conversion rate (in challenged and unchallenged chickens).

The invention relates to the following aspect with respect to *Bacillus subtilis* subspecies and *Bacillus* strain(s):

Aspect 1: A *Bacillus subtilis* subspecies or one or more *Bacillus* strain(s) comprising one or more of the features selected from the group consisting of i) a gyrB gene with at least 94.7% sequence identity to SEQ ID NO: 1 or a gyrB gene product with at least 99.4% sequence identity to SEQ ID NO: 2;

ii) a rpoB gene with at least 96.6% sequence identity to SEQ ID NO: 3 or an rpoB gene product with at least 99.7% sequence identity to SEQ ID NO: 4;

iii) a gyrA gene with at least 89.5% sequence identity to SEQ ID NO: 7 or a gyrA gene product with at least 97.4% sequence identity to SEQ ID NO: 8; and iv) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises a gyrB gene with at least 94.7% sequence identity to SEQ ID NO: 1 such as at least 94.8%, such as at least 95%, such as at least 96%, such as at least 97%, such as at least 98% and such as at least 99% sequence identity.

In one embodiment of Aspect 1 the *Bacillus subtilis* subspecies or the one or more *Bacillus* strain(s) comprises a gyrB gene product with at least 99.4% sequence identity to SEQ ID NO: 2 such as at least 99.5%, such as at least 99.6%, such as at least 99.7%, such as at least 99.8% and such as at least 99.9% sequence identity.

In one embodiment of Aspect 1 the *Bacillus subtilis* subspecies or the one or more *Bacillus* strain(s) comprises an rpoB gene with at least 96.6% sequence identity to SEQ ID NO: 3 such as at least 96.8%, such as at least 97%, such as at least 98% and such as at least 99% sequence identity.

In one embodiment of Aspect 1 the *Bacillus subtilis* subspecies or the one or more *Bacillus* strain(s) comprises an rpoB gene product with at least 99.7% sequence identity to SEQ ID NO: 4 such as at least 99.75%, such as at least 99.8% and such as 99.9% sequence identity.

In one embodiment of Aspect 1 the *Bacillus subtilis* subspecies or the one or more *Bacillus* strain(s) comprises a gyrA gene product with at least 97.4% sequence identity to SEQ ID NO: 8 such as at least 97.6%, such as at least 97.8%, such as at least 98%, such as at least 99% and such as at least 99.5% sequence identity.

In one embodiment of Aspect 1 the *Bacillus subtilis* subspecies or the one or more *Bacillus* strain(s) comprises a gyrA gene with at least 89.5% sequence identity to SEQ ID NO: 7 such as at least 90%, such as at least 91%, such as at least 92%, such as at least 93%, such as at least 94%, such as at least 95%, such as at least 96%, such as at least 97%, such as at least 98% and such as at least 99% sequence identity.

In one embodiment of Aspect 1 the *Bacillus subtilis* subspecies or the one or more *Bacillus* strain(s) comprises a genome with an Average Nucleotide Identity to the genome sequence of DSM 29870 of at least 95%, such as at least 96%, such as at least 97%, such as at least 98%, such as at least 99% sequence identity.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) a gyrA gene with at least 89.5% sequence identity to SEQ ID NO: 7 or a gyrA gene product with at least 97.4% sequence identity to SEQ ID NO: 8 and ii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a gyrA gene with at least 89.5% sequence identity to SEQ ID NO: 7 or a gyrA gene product with at least 97.4% sequence identity to SEQ ID NO: 8.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 1 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a gyrA gene with at least 89.5% sequence identity to SEQ ID NO: 7 or a gyrA gene product with at least 97.4% sequence identity to SEQ ID NO: 8 and iv) a genome with an Average Nucleotide Identity to the genome sequence of DSM 29870 of at least 95%.

In one embodiment, the *Bacillus subtilis* subspecies or the one or more *Bacillus* strain(s) according to Aspect 1 or any of the above embodiments is non-hemolytic (e.g., determined as described in Example 8).

In a preferred embodiment the *Bacillus subtilis* subspecies or the one or more *Bacillus* strain(s) according to Aspect 1 or any of the above embodiments has a high compatibility with monensin such as being compatible with at least 2.3

μg/ml monensin as determined in Example 12. It is even more preferred that the *Bacillus subtilis* subspecies is compatible with at least 2.4 μg/ml monensin as determined in Example 12 (such as at least 2.5 μg/ml monensin as determined in Example 12, such as at least 2.6 μg/ml monensin as determined in Example 12 or such as at least 2.7 μg/ml monensin as determined in Example 12).

In one embodiment, the *Bacillus subtilis* subspecies or the one or more *Bacillus* strain(s) according to Aspect 1 or any of the above embodiments has antimicrobial activity against *Clostridium perfringens*. The effect against *Clostridium perfringens* can be determined as described in Example 6.

In one embodiment, the *Bacillus subtilis* subspecies or the one or more *Bacillus* strain(s) according to Aspect 1 or any of the above embodiments has antimicrobial activity against *E. coli*. The effect against *E. coli* can be determined as described in Example 7.

In one embodiment, the *Bacillus subtilis* subspecies or the one or more *Bacillus* strain(s) according to Aspect 1 or any of the above embodiments has antimicrobial activity against *Clostridium perfringens* and *E. coli*.

In one embodiment, the *Bacillus subtilis* subspecies or the one or more *Bacillus* strain(s) according to Aspect 1 or any of the above embodiments is sensitive to Vancomycin, Clindamycin, Chloramphenicol, Gentamicin, Kanamycin, Streptomycin, Erythromycin and Tetracycline (e.g., as determined as described in Example 9).

In one embodiment, the *Bacillus subtilis* subspecies or the one or more *Bacillus* strain(s) according to Aspect 1 or any of the above embodiments has a 16S rDNA with more than 98% (such as more than 98.5%, such as more than 99%, such as more than 99.5%) sequence identity to SEQ ID NO: 9.

In one embodiment, the *Bacillus subtilis* subspecies or the one or more *Bacillus* strain(s) according to Aspect 1 or any of the above embodiments is a *Bacillus subtilis* strain.

The *Bacillus subtilis* subspecies or the one or more *Bacillus* strain(s) according to Aspect 1 or any of the above embodiments is in one embodiment the *Bacillus* strain having deposit accession number DSM 29870, or a strain having all of the identifying characteristics of *Bacillus* DSM 29870 or a mutant thereof that has antimicrobial activity against *Clostridium perfringens*. In a further embodiment, the *Bacillus subtilis* subspecies or the one or more *Bacillus* strain(s) according to Aspect 1 or any of the above embodiments is the *Bacillus* strain having deposit accession number DSM 29870.

The invention relates in one embodiment to a *Bacillus* having deposit accession number DSM 29870 or a strain having all of the identifying characteristics of *Bacillus* DSM 29870 or a mutant thereof. In an embodiment, the invention relates to a *Bacillus* having deposit accession number DSM 29870.

The invention also relates to a biologically pure culture of the *Bacillus* strain according to Aspect 1. In a further embodiment the invention relates to a biologically pure culture of the *Bacillus* strain having deposit accession number DSM 29870 or a strain having all of the identifying characteristics of *Bacillus* DSM 29870 or a mutant thereof. In a further embodiment, the invention relates to a biologically pure culture of the *Bacillus* strain having deposit accession number DSM 29870.

The invention also relates to an isolated *Bacillus* strain according to Aspect 1. In a further embodiment the invention also relates to an isolated *Bacillus* strain having deposit accession number DSM 29870 or an isolated strain having all of the identifying characteristics of *Bacillus* DSM 29870 or a mutant thereof.

The invention also relates to a spore of *Bacillus* strain according to Aspect 1. In a further embodiment the invention also relates to a spore of *Bacillus* strain having deposit accession number DSM 29870 or a spore having all of the identifying characteristics of *Bacillus* DSM 29870 or a mutant thereof. The spore is preferably a stable spore.

The invention relates to a composition comprising spores (such as stable spores) of the *Bacillus subtilis* subspecies or the one or more *Bacillus* strain(s) according to the invention.

More specifically the invention relates to the following aspects with respect to compositions comprising the *Bacillus subtilis* subspecies or the *Bacillus* strain(s):

Aspect 2: A composition comprising a *Bacillus subtilis* subspecies or one or more *Bacillus* strain(s) comprising one or more of the features selected from the group consisting of:

i) a gyrB gene with at least 94.7% sequence identity to SEQ ID NO: 1 or a gyrB gene product with at least 99.4% sequence identity to SEQ ID NO: 2;
ii) a rpoB gene with at least 96.6% sequence identity to SEQ ID NO: 3 or an rpoB gene product with at least 99.7% sequence identity to SEQ ID NO: 4;
iii) a gyrA gene with at least 89.5% sequence identity to SEQ ID NO: 7 or a gyrA gene product with at least 97.4% sequence identity to SEQ ID NO: 8; and
iv) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises a gyrB gene with at least 94.7% sequence identity to SEQ ID NO: 1 such as at least 94.8%, such as at least 95%, such as at least 96%, such as at least 97%, such as at least 98% and such as at least 99% sequence identity.

In one embodiment of Aspect 2 the *Bacillus subtilis* subspecies or the one or more *Bacillus* strain(s) comprises a gyrB gene product with at least 99.4% sequence identity to SEQ ID NO: 2 such as at least 99.5%, such as at least 99.6%, such as at least 99.7%, such as at least 99.8% and such as at least 99.9% sequence identity.

In one embodiment of Aspect 2 the *Bacillus subtilis* subspecies or the one or more *Bacillus* strain(s) comprises an rpoB gene with at least 96.6% sequence identity to SEQ ID NO: 3 such as at least 96.8%, such as at least 97%, such as at least 98% and such as at least 99% sequence identity.

In one embodiment of Aspect 2 the *Bacillus subtilis* subspecies or the one or more *Bacillus* strain(s) comprises an rpoB gene product with at least 99.7% sequence identity to SEQ ID NO: 4 such as at least 99.75%, such as at least 99.8% and such as 99.9% sequence identity.

In one embodiment of Aspect 2 the *Bacillus subtilis* subspecies or the one or more *Bacillus* strain(s) comprises a gyrA gene product with at least 97.4% sequence identity to SEQ ID NO: 8 such as at least 97.6%, such as at least 97.8%, such as at least 98%, such as at least 99% and such as at least 99.5% sequence identity.

In one embodiment of Aspect 2 the *Bacillus subtilis* subspecies or the one or more *Bacillus* strain(s) comprises a gyrA gene with at least 89.5% sequence identity to SEQ ID NO: 7 such as at least 90%, such as at least 91%, such as at least 92%, such as at least 93%, such as at least 94%, such as at least 95%, such as at least 96%, such as at least 97%, such as at least 98% and such as at least 99% sequence identity.

In one embodiment of Aspect 2 the *Bacillus subtilis* subspecies or the one or more *Bacillus* strain(s) comprises a genome with an Average Nucleotide Identity to the genome sequence of DSM 29870 of at least 95%, such as at least 96%, such as at least 97%, such as at least 98%, such as at least 99% sequence identity.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a genome with an Average Nucleotide Identity to the genome sequence of DSM 29870 of at least 95%.

In one embodiment of Aspect 2 the composition comprising a *Bacillus subtilis* subspecies or the one or more *Bacillus* strain(s) comprises:

i) a gyrA gene with at least 89.5% sequence identity to SEQ ID NO: 7 or a gyrA gene product with at least 97.4% sequence identity to SEQ ID NO: 8 and ii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a gyrA gene with at least 89.5% sequence identity to SEQ ID NO: 7 or a gyrA gene product with at least 97.4% sequence identity to SEQ ID NO: 8.

In one embodiment of Aspect 2 the composition comprising a *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) an rpoB gene with at least 96.6% sequence identity to SEQ ID NO: 3 or an rpoB gene product with at least 99.7% sequence identity to SEQ ID NO: 4 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) an rpoB gene with at least 96.6% sequence identity to SEQ ID NO: 3 or an rpoB gene product with at least 99.7% sequence identity to SEQ ID NO: 4 and ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

In one embodiment of Aspect 2 the *Bacillus subtilis* subspecies or the one or more *Bacillus* strain(s) comprises:

i) a gyrB gene with at least 94.7% sequence identity to SEQ ID NO: 1 or a gyrB gene product with at least 99.4% sequence identity to SEQ ID NO: 2 or ii) an rpoB gene with at least 96.6% sequence identity to SEQ ID NO: 3 or an rpoB gene product with at least 99.7% sequence identity to SEQ ID NO: 4 or iii) a gyrA gene with at least 89.5% sequence identity to SEQ ID NO: 7 or a gyrA gene product with at least 97.4% sequence identity to SEQ ID NO: 8 or iv) a genome with an Average Nucleotide Identity to the genome sequence of DSM 29870 of at least 95%.

In one embodiment of Aspect 2 the *Bacillus subtilis* subspecies or the one or more *Bacillus* strain(s) are non-hemolytic (e.g., determined as described in Example 8).

In a preferred embodiment of Aspect 2 the *Bacillus subtilis* subspecies or the one or more *Bacillus* strain(s) has a high compatibility with monensin such as being compatible with at least 2.3 μg/ml monensin as determined in Example 12. It is even more preferred that the *Bacillus subtilis* subspecies is compatible with at least 2.4 μg/ml monensin as determined in Example 12 (such as at least 2.5 μg/ml monensin as determined in Example 12, such as at least 2.6 μg/ml monensin as determined in Example 12 or such as at least 2.7 μg/ml monensin as determined in Example 12).

In one embodiment of Aspect 2 the *Bacillus subtilis* subspecies or the one or more *Bacillus* strain(s) have antimicrobial activity, e.g., against *Clostridium perfringens*. The effect against *Clostridium perfringens* can be determined as described in Example 6.

In one embodiment of Aspect 2 the *Bacillus subtilis* subspecies or the one or more *Bacillus* strain(s) have antimicrobial activity against *E. coli*. The effect against *E. coli* can be determined as described in Example 7.

In one embodiment of Aspect 2 the *Bacillus subtilis* subspecies or the one or more *Bacillus* strain(s) have antimicrobial activity against *Clostridium perfringens* and *E. coli*.

In one embodiment of Aspect 2 the *Bacillus subtilis* subspecies or the one or more *Bacillus* strain(s) is sensitive to Vancomycin, Clindamycin, Chloramphenicol, Gentamicin, Kanamycin, Streptomycin, Erythromycin and Tetracycline (e.g., as determined as described in Example 9).

In one embodiment, the *Bacillus subtilis* subspecies or the one or more *Bacillus* strain(s) according to Aspect 2 or any of the above embodiments has a 16S rDNA with more than 98% (such as more than 98.5%, such as more than 99%, such as more than 99.5%) sequence identity to SEQ ID NO: 9.

In one embodiment, the *Bacillus subtilis* subspecies or the one or more *Bacillus* strain(s) according to Aspect 2 or any of the above embodiments is a *Bacillus subtilis* strain.

In one embodiment, the *Bacillus subtilis* subspecies or the one or more *Bacillus* strain(s) according to Aspect 2 or any of the above embodiments can in one embodiment be the *Bacillus* strain having deposit accession number DSM 29870, or a strain having all of the identifying characteristics of *Bacillus* DSM 29870 or a mutant thereof that has antimicrobial activity against *Clostridium perfringens*.

The invention relates in one embodiment to a composition comprising a *Bacillus* having deposit accession number DSM 29870 or a strain having all of the identifying characteristics of *Bacillus* DSM 29870 or a mutant thereof.

The invention also relates to a composition comprising a biologically pure culture of the *Bacillus* strain according to Aspect 2. In a further embodiment the invention relates to a composition comprising a biologically pure culture of the *Bacillus* strain having deposit accession number DSM 29870 or a strain having all of the identifying characteristics of *Bacillus* DSM 29870 or a mutant thereof.

The invention also relates to a composition comprising an isolated *Bacillus* strain according to Aspect 2. In a further embodiment the invention also relates to a composition comprising an isolated *Bacillus* strain having deposit accession number DSM 29870 or an isolated strain having all of the identifying characteristics of *Bacillus* DSM 29870 or a mutant thereof.

In one embodiment of Aspect 2 the *Bacillus* spores of the composition are present as dried spores (such as, e.g., spray-dried spores). In one embodiment of Aspect 2 the *Bacillus* spores of the composition are present as stable spores. The composition according to Aspect 2 can also be a liquid composition and/or comprise culture supernatant comprising the *Bacillus* strain(s) of the invention.

In one embodiment of Aspect 2 the composition further comprises a carrier. The carrier can comprise one or more of the following compounds: water, glycerol, ethylene glycol, 1,2-propylene glycol or 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, cellulose farigel, cassava cores, sodium aluminium silicate, colloidal amorphous silica, Sipernat 50S, polyethylene glycol 200, polyethylene glycol 400, polyethylene glycol 600, polyethylene glycol 1000, polyethylene glycol 1500, polyethylene glycol 4000 and carbopol.

In a preferred embodiment of Aspect 2 the composition further comprises calcium carbonate and sodium aluminium silicate.

In a preferred embodiment of Aspect 2 the composition further comprises Calcium carbonate, sodium aluminium silicate and sucrose.

In another preferred embodiment of Aspect 2 the composition further comprises one or more carriers such as one or more carriers selected from the group consisting of Calcium carbonate, sodium sulphate, starch, farigel and cassava cores.

In another preferred embodiment of Aspect 2 the composition further comprises one or more flowability agents such as sodium aluminium silicate and/or colloidal amorphous silica (e.g., Sipernat 50S).

In another preferred embodiment of Aspect 2 the composition further comprises one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In a preferred embodiment the composition comprises *Bacillus* DSM 29870, calcium carbonate and sodium aluminium silicate.

In a preferred embodiment the composition comprises *Bacillus* DSM 29870, Calcium carbonate, sodium aluminium silicate and sucrose.

In a preferred embodiment the composition comprises *Bacillus* DSM 29870 and one or more carriers such as one or more carriers selected from the group consisting of Calcium carbonate, sodium sulphate, starch, farigel and cassava cores.

In a preferred embodiment the composition comprises *Bacillus* DSM 29870 and one or more flowability agents such as sodium aluminium silicate and/or colloidal amorphous silica (e.g., Sipernat 50S).

In a preferred embodiment the composition comprises *Bacillus* DSM 29870 and one or more binder such as one or more binders selected from the group consisting of sucrose, sorbitol, glycerol, polyethylene glycol 200, polyethylene glycol 400, polyethylene glycol 600, polyethylene glycol 1000, polyethylene glycol 1500, polyethylene glycol 4000, dextrin, maltodextrin and carbopol.

In one embodiment the composition comprises one or more coccidiostats wherein the composition, e.g., is a premix.

In a preferred embodiment the composition according to Aspect 2 the composition comprises from $10^5$ to $10^{12}$ CFU/g of isolated *Bacillus* spores such as from $10^5$ to $10^7$ CFU/g of isolated *Bacillus* spores, such as $10^7$ to $10^9$ CFU/g of isolated *Bacillus* spores, such as from $10^9$ to $10^{11}$ CFU/g of isolated *Bacillus* spores, such as $10^{11}$ to $10^{12}$ CFU/g of isolated *Bacillus* spores or any combination of these intervals.

In yet another preferred embodiment the composition according to Aspect 2 is an animal feed such as an animal feed additive. In one embodiment the animal feed is characterized in that at least 70% (such as at least 80% or at least 90%) of the *Bacillus* spores survive gastric stability in a mono-gastric animal such as chickens.

The composition according to Aspect 2 can be an animal feed which further comprises one or more components selected from the list consisting of: one or more enzymes; one or more additional microbes; one or more vitamins; one or more minerals; one or more amino acids; and one or more other feed ingredients.

The composition according to Aspect 2 can be an animal feed or an animal feed additive wherein the bacterial count of each *Bacillus* spore is $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

The composition according to Aspect 2 can be a mono-gastric animal feed. The mono-gastric animal can be selected from the group consisting of pigs, swine, piglets, sows, poultry, turkeys, ducks, chicken, broilers, layers, chicks, fish and crustaceans. In one embodiment the animal is not a human being. Mono-gastric animals include in one embodiment, but are not limited to, pigs or swine (including, but not limited to, piglets, growing pigs, and sows); poultry such as turkeys, ducks and chicken (including but not limited to broilers, chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In a preferred embodiment, the composition according to Aspect 2 is an animal feed or animal feed additive wherein the *Bacillus* strain improves gut health of chickens with infection of *Clostridium perfringens* by having antimicrobial activity against *Clostridium perfringens*.

In a preferred embodiment, the composition according to Aspect 2 is an animal feed or animal feed additive for treatment of necrotic enteritis or treatment of a *Clostridium perfringens* infection (e.g., for treatment of mono-gastric animals including swine and poultry such as chickens).

In an embodiment to any of the aforementioned embodiments, the *Bacillus* spore kills/inhibits at least 40% (such as at least 45%, at least 50%, at least 60%, at least 70% or at least 80%) of *Clostridium perfringens* after 24 hours, e.g., determined as described in Example 6.

In another embodiment of the invention, the composition such as the animal feed further comprises concentrate. In another embodiment of the invention the composition such as the animal feed further comprises forage. In another embodiment of the invention the composition such as the animal feed further comprises one or more additional microbes. In another embodiment of the invention the composition such as the animal feed further comprises one or more enzymes. In another embodiment of the invention the composition such as the animal feed further comprises one or more vitamins. In another embodiment of the invention the composition such as the animal feed further comprises one or more minerals. In another embodiment of the invention the composition such as the animal feed further comprises one or more amino acids. In another embodiment of the invention the composition such as the animal feed further comprises one or more other feed ingredients.

In an embodiment to any of the aforementioned embodiments, the composition also improves the health of the mono-gastric animal when fed to said animal. In another embodiment to any of the aforementioned embodiments, the composition also increases the egg yield of poultry when fed to said poultry. In an embodiment to any of the aforementioned embodiments, the composition increases the meat yield of the mono-gastric animal when fed to said animal.

In a preferred embodiment, the composition such as the animal feed comprises one or more bacterial strains described herein, wherein the bacterial count of each of the bacterial strains is between $1\times10^4$ and $1\times10^{18}$ CFU/kg of composition, preferably between $1\times10^7$ and $1\times10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of composition.

In a preferred embodiment, the bacterial count of each of the bacterial strains in the animal feed additive is between $1\times10^4$ and $1\times10^{18}$ CFU/kg of composition, preferably between $1\times10^7$ and $1\times10^{16}$ CFU/kg of composition, more preferably between $1\times10^{10}$ and $1\times10^{15}$ CFU/kg of composition and most preferably between $1\times10^{11}$ and $1\times10^{14}$ CFU/kg of dry matter.

In a preferred embodiment, the bacterial count of each of the bacterial strains in the animal feed is between $1\times10^4$ and $1\times10^{14}$ CFU/kg of dry matter, preferably between $1\times10^6$ and $1\times10^{12}$ CFU/kg of dry matter, and more preferably between $1\times10^7$ and $1\times10^{11}$ CFU/kg of dry matter. In a more preferred embodiment the bacterial count of each of the bacterial strains in the animal feed composition is between $1\times10^8$ and $1\times10^{10}$ CFU/kg of dry matter.

In a preferred embodiment, the composition such as the animal feed has a bacterial count of each *Bacillus* spore between $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

In still yet another embodiment of the invention, the one or more bacterial strains are present in the composition in form of a spore such as a stable spore. In still a further embodiment of the invention, the stable spore will germinate in the intestine and/or stomach of the mono-gastric animal.

In one embodiment, the one or more bacterial strains are stable when subjected to pressures applied/achieved during an extrusion process for pelleting. In a particular embodiment, the one or more bacterial strains are stable at pressures ranging from 1 bar to 40 bar, particularly 10 bar to 40 bar, more particularly 15 bar to 40 bar, even more particularly 20 bar to 40 bar, still even more particularly 35 bar to 37 bar, even still more particularly 36 bar.

In a particular embodiment, the one or more bacterial strains are stable at high temperatures. In particular, the bacterial strains are stable when they are subjected to temperatures achieved during an extrusion process for pelleting. In an even more particular embodiment, the one or more bacterial strains are stable at temperatures ranging from 80° C. to 120° C., particularly temperatures ranging from, 90° C. to 120° C., even more particularly temperatures ranging from 95° C. to 120° C.

In another aspect, the invention relates to a composition such as an animal feed composition comprising a carrier, such as forage and one or more of the bacteria cultures having characteristics substantially identical to that of the strain having the deposit accession number DSM 29870.

In an embodiment, the animal feed composition comprises a carrier and the strain having the deposit accession number DSM 29870, or a strain having all of the identifying characteristics of *Bacillus* DSM 29870 or a mutant thereof.

In another embodiment, the animal feed composition is for feeding to a mono-gastric animal. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

In an embodiment, the animal feed composition further comprises one or more additional microbes. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and Megasphaera or any combination thereof.

In a particular embodiment, animal feed composition further comprises a bacterium from one or more of the following strains of *Bacillus amyloliquefaciens, Bacillus subtilis, Bacillus pumilus, Bacillus polymyxa, Bacillus licheniformis, Bacillus megaterium, Bacillus coagulans, Bacillus circulans*, or any combination thereof.

In a particular embodiment, the animal feed composition further comprises one or more types of yeast. The one or more types of yeast can be selected from the group consisting of Saccharomycetaceae, *Saccharomyces* (such as *S. cerevisiae* and/or *S. boulardii*), *Kluyveromyces* (such as *K. marxianus* and *K. lactis*), *Candida* (such as *C. utilis*, also called Torula yeast), *Pichia* (such as *P. pastoris*), *Torulaspora* (such as *T. delbrueckii*), *Phaffia* yeasts and Basidiomycota.

In an embodiment to any of the aforementioned embodiments the composition further comprises a carrier. The carrier can comprise one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol. and cellulose.

Animal Feed

In one aspect, the animal feed comprising the *Bacillus subtilis* subspecies or the *Bacillus* strain(s) according to Aspect 1 or the *Bacillus* strain having deposit accession number DSM 29870, or a strain having all of the identifying characteristics of *Bacillus* DSM 29870 or a mutant of DSM 29870 and further comprises one or more of concentrate(s), vitamin(s), mineral(s), enzyme(s), amino acid(s) and/or other feed ingredient(s) (such as in a premix). In a specific embodiment the animal feed further comprises forage.

Forage as defined herein also includes roughage. Forage is fresh plant material such as hay and silage from forage plants, grass and other forage plants, grass and other forage plants, seaweed, sprouted grains and legumes, or any combination thereof. Examples of forage plants are Alfalfa (lucerne), birdsfoot trefoil, brassica (e.g., kale, rapeseed (canola), rutabaga (swede), turnip), clover (e.g., alsike clover, red clover, subterranean clover, white clover), grass (e.g., Bermuda grass, brome, false oat grass, fescue, heath grass, meadow grasses, orchard grass, ryegrass, Timothy-grass), corn (maize), millet, barley, oats, rye, sorghum, soybeans and wheat and vegetables such as beets. Crops suitable for ensilage are the ordinary grasses, clovers, alfalfa, vetches, oats, rye and maize. Forage further includes crop residues from grain production (such as corn stover; straw from wheat, barley, oat, rye and other grains); residues from vegetables like beet tops; residues from oilseed production like stems and leaves form soy beans, rapeseed and other legumes; and fractions from the refining of grains for animal or human consumption or from fuel production or other industries.

Roughage is generally dry plant material with high levels of fiber, such as fiber, bran, husks from seeds and grains and crop residues (such as stover, copra, straw, chaff, sugar beet waste).

Examples of concentrates are feed with high protein and energy concentrations, such as fish meal, molasses, oligosaccharides, sorghum, seeds and grains (either whole or prepared by crushing, milling, etc. from, e.g., corn, oats, rye, barley, wheat), oilseed press cake (e.g., from cottonseed, safflower, sunflower, soybean (such as soybean meal), rapeseed/canola, peanut or groundnut), palm kernel cake, yeast derived material and distillers grains (such as wet distillers grains (WDS) and dried distillers grains with solubles (DDGS)).

In one embodiment, the forage and one or more microbes are mixed with a concentrate. In another embodiment, the forage and one or more microbes are mixed with a premix. In a further embodiment, the forage and one or more microbes are mixed with vitamins and/or minerals. In a further embodiment, the forage and one or more microbes are mixed with one or more enzymes. In a further embodiment, the forage and one or more microbes are mixed with other feed ingredients, such as colouring agents, stabilisers, growth improving additives and aroma compounds/flavorings, polyunsaturated fatty acids (PUFAs); reactive oxygen generating species, anti-microbial peptides, anti-fungal polypeptides and amino acids.

In particular embodiments, the animal feed may comprise *Bacillus* stain DSM 29870 or a strain having all of the identifying characteristics of *Bacillus* DSM 29870 or a mutant of DSM 29870 and 0-80% maize; and/or 0-80% sorghum; and/or 0-70% wheat; and/or 0-70% barley; and/or 0-30% oats; and/or 0-40% soybean meal; and/or 0-10% fish meal; and/or 0-20% whey.

The animal feed may comprise *Bacillus* stain DSM 29870 or a strain having all of the identifying characteristics of *Bacillus* DSM 29870 or a mutant of DSM 29870 and vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Cruciferaceae, Chenopodiaceae, and Poaceae, such as soy bean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Chenopodiaceae, e.g., beet, sugar beet, spinach or quinoa. Other examples of vegetable protein sources are rapeseed, and cabbage. In another particular embodiment, soybean is a preferred vegetable protein source. Other examples of vegetable protein sources are cereals such as barley, wheat, rye, oat, maize (corn), rice, and sorghum.

In a particular embodiment the animal feed consists of or comprises milk (e.g., from sow), e.g., for feeding of piglets. In another particular embodiment the animal feed consists of or comprises milk replacement, e.g., for feeding of piglets.

Premix

In an embodiment, the animal feed may include a premix, comprising, e.g., vitamins, minerals, enzymes, preservatives, antibiotics, other feed ingredients or any combination thereof which are mixed into the animal feed.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

Enzymes

In another embodiment, the animal feed compositions or animal feed additive described herein optionally include one or more enzymes. Enzymes can be classified on the basis of the handbook Enzyme Nomenclature from NC-IUBMB, 1992), see also the ENZYME site at the internet: expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch, 2000, The ENZYME database, *Nucleic Acids Res.* 28: 304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, xylanase, galactanase, mannanase, dextranase and alpha-galactosidase, in families based on amino acid sequence similarities has been proposed a few years ago. They currently fall into 90 different families: See the CAZy(ModO) internet site (Coutinho and Henrissat, 1999, Carbohydrate-Active Enzymes server at URL: afmb.cnrs-mrs.fr/~cazy/CAZY/index.html (corresponding papers: Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12; Coutinho, P. M. & Henrissat, B. (1999) The modular structure of cellulases and other carbohydrate-active enzymes: an integrated database approach. In "Genetics, Biochemistry and Ecology of Cellulose Degradation"., K. Ohmiya, K. Hayashi, K. Sakka, Y. Kobayashi, S. Karita and T. Kimura eds., Uni Publishers Co., Tokyo, pp. 15-23).

Thus the composition of the invention may also comprise at least one other enzyme selected from the group comprising of phytase (EC 3.1.3.8 or 3.1.3.26); xylanase (EC 3.2.1.8); galactanase (EC 3.2.1.89); alpha-galactosidase (EC 3.2.1.22); protease (EC 3.4); phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); amylase such as, for example, alpha-amylase (EC 3.2.1.1); lysozyme (EC 3.2.1.17); and beta-glucanase (EC 3.2.1.4 or EC 3.2.1.6), or any mixture thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P and HiPhos™ (DSM Nutritional Products), Natuphos™ (BASF), Finase® and Quantum® Blue (AB Enzymes), the Phyzyme® XP (Verenium/DuPont) and Axtra® PHY (DuPont). Other preferred phytases include those described in, e.g., WO 98/28408, WO 00/43503, and WO 03/066847.

In a particular embodiment, the composition of the invention comprises a xylanase (EC 3.2.1.8). Examples of commercially available xylanases include Ronozyme® WX and G2 (DSM Nutritional Products), Econase® XT and Barley (AB Vista), Xylathin® (Verenium) and Axtra® XB (Xylanase/beta-glucanase, DuPont)

In a particular embodiment, the composition of the invention comprises a protease (EC 3.4). Examples of commercially available proteases include Ronozyme® ProAct (DSM Nutritional Products).

Amino Acids

The composition of the invention may further comprise one or more amino acids. Examples of amino acids which are used in animal feed are lysine, alanine, beta-alanine, threonine, methionine and tryptophan.

Other Feed Ingredients

The composition of the invention may further comprise colouring agents, stabilisers, growth improving additives and aroma compounds/flavorings, polyunsaturated fatty acids (PUFAs); reactive oxygen generating species, antimicrobial peptides and anti-fungal polypeptides.

Examples of colouring agents are carotenoids such as beta-carotene, astaxanthin, and lutein.

Examples of aroma compounds/flavorings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are C18, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a syntethase.

The composition of the invention may further comprise at least one amino acid. Examples of amino acids which are used in animal feed are lysine, alanine, beta-alanine, threonine, methionine and tryptophan.

Manufacturing

Animal diets can, e.g., be manufactured as mash feed (non-pelleted) or pelleted feed. Typically, the milled feedstuffs are mixed and sufficient amounts of essential vitamins and minerals are added according to the specifications for the species in question. The bacteria cultures and optionally enzymes can be added as solid or liquid formulations. For example, for mash feed a solid or liquid culture formulation may be added before or during the ingredient mixing step. For pelleted feed the (liquid or solid) culture preparation may also be added before or during the feed ingredient step.

Typically a liquid culture preparation comprises the culture of the invention optionally with a polyol, such as glycerol, ethylene glycol or propylene glycol, and is added after the pelleting step, such as by spraying the liquid formulation onto the pellets. The enzyme may also be incorporated in a feed additive or premix.

The enzyme may be added to the feed mix as a granule, which is optionally pelleted or extruded. The granule typically comprises a core particle and one or more coatings, which typically are salt and/or wax coatings. The core particle can either be a homogeneous blend of an active compound optionally together with salts (e.g., organic or inorganic zinc or calcium salt) or an inert particle with an active compound applied onto it. The active compound is the culture of the invention optionally combined with one or more enzymes. The inert particle may be water soluble or water insoluble, e.g., starch, a sugar (such as sucrose or lactose), or a salt (such as NaCl, $Na_2SO_4$). The salt coating is typically at least 1 μm thick and can either be one particular salt or a mixture of salts, such as $Na_2SO_4$, $K_2SO_4$, $MgSO_4$ and/or sodium citrate. Other examples are those described in, e.g., WO 2008/017659, WO 2006/034710, WO 97/05245, WO 98/54980, WO 98/55599, WO 00/70034 or polymer coating such as described in WO 01/00042.

Alternatively, the protease can be prepared by freezing a mixture of liquid culture solution with a bulking agent such as ground soybean meal, and then lyophilizing the mixture.

In one embodiment, the invention relates to a method for treatment of *C. perfringens* infections and/or necrotic enteritis in an animal such as a mono-gastric animal including poultry using the composition according to Aspect 2. In one embodiment the animal is not a human being. In a further embodiment, animal feed comprising the *Bacillus* strains according to Aspect 1 is fed to a mono-gastric animal in an effective amount. Mono-gastric animals include, but are not limited to, pigs or swine (including, but not limited to, piglets, growing pigs, and sows); poultry such as turkeys, ducks and chicken (including but not limited to broiler chicks, layers); horses (including but not limited to hotbloods, coldbloods and warm bloods) and fish (including but not limited to salmon, trout, tilapia, catfish and carps; and crustaceans (including but not limited to shrimps and prawns). Pigs and/or poultry are preferred mono-gastric animals.

The animal feed can further comprise one or more components selected from the list consisting of concentrate; forage; one or more enzymes; one or more additional microbes; one or more vitamins; one or more minerals; one or more amino acids; and one or more other feed ingredients.

In one embodiment, the method comprises administering to the animal feed the *Bacillus* strains having the deposit accession number DSM 29870 or a strain having all the identifying characteristics of *Bacillus* DSM 29870 or a mutant thereof in an effective amount.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In an embodiment to any of the aforementioned embodiments, the method also improves the health of the mono-gastric animal feed. In another embodiment to any of the aforementioned embodiments, the method also increases the egg yield of poultry. In an embodiment to any of the aforementioned embodiments, the method also increases the meat yield of the mono-gastric animal.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of animal feed. In a more preferred embodiment the bacterial count of each of the bacterial strains described herein is between $1\times10^8$ and $1\times10^{10}$ CFU/kg of animal feed.

In a preferred embodiment, the method comprises administering to a mono-gastric animal one or more bacterial strains described herein, wherein the bacterial count of each of the bacterial strains is between $1\times10^3$ and $1\times10^{13}$ CFU/animal/day, preferably between $1\times10^5$ and $1\times10^{11}$ CFU/animal/day, more preferably between $1\times10^6$ and $1\times10^{10}$ CFU/animal/day and most preferably between $1\times10^7$ and $1\times10^9$ CFU/animal/day.

In another aspect, the invention covers the method for treatment of *C. perfringens* infections comprising:

(a) feeding a mono-gastric animal a feed; and (b) administering to an animal the strain having the deposit accession number DSM 29870; or a strain having all the identifying characteristics of *Bacillus* DSM 29870 or a mutant thereof;

wherein the *Bacillus* strain antimicrobial activity against *Clostridium perfringens*, and wherein step (a) occurs before, after, or simultaneously with step (b).

In a preferred embodiment of the method, the animal feed is fed to a mono-gastric animal. In an embodiment of the method, the mono-gastric animal is, e.g., pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), or fish (including but not limited to salmon, trout, tilapia, catfish and carps; and crustaceans (including but not limited to shrimps and prawns). Pigs and/or poultry are preferred mono-gastric animals.

In another embodiment of the method, the animal feed further comprises one or more components selected from the list consisting of concentrate; forage; one or more enzymes; one or more additional microbes; one or more vitamins; one or more minerals; one or more amino acids; and one or more other feed ingredients.

In another embodiment of the method, the animal feed further comprises concentrate. In another embodiment of the method, the animal feed further comprises forage. In another embodiment of the method, the animal feed further comprises one or more additional microbes. In another embodiment of the method, the animal feed further comprises one or more enzymes. In another embodiment of the method, the animal feed further comprises one or more vitamins. In another embodiment of the method, the animal feed further comprises one or more minerals. In another embodiment of the method, the animal feed further comprises one or more amino acids. In another embodiment of the method, the animal feed further comprises one or more other feed ingredients.

In still yet another embodiment of the method, the one or more bacterial strains are present in the form of a stable spore. In still a further embodiment of the method, the stable spore will germinate in the rumen of the ruminant.

In a preferred embodiment, the method comprises administering to a mono-gastric animal one or more bacterial strains described herein, wherein the bacterial count of each of the bacterial strains is between $1\times10^4$ and $1\times10^{14}$ CFU/kg of forage, preferably between $1\times10^6$ and $1\times10^{12}$ CFU/kg of forage, and more preferably between $1\times10^7$ and $1\times10^{11}$ CFU/kg of forage. In a more preferred embodiment the bacterial count of each of the bacterial strains described herein is between $1\times10^8$ and $1\times10^{10}$ CFU/kg of forage.

In a preferred embodiment, the method comprises administering to a mono-gastric animal one or more bacterial strains described herein, wherein the bacterial count of each of the bacterial strains is between $1\times10^5$ and $1\times10^{15}$ CFU/animal/day, preferably between $1\times10^7$ and $1\times10^{13}$ CFU/animal/day, and more preferably between $1\times10^8$ and $1\times10^{12}$ CFU/animal/day. In a more preferred embodiment the bacterial count of each of the bacterial strains described herein is between $1\times10^9$ and $1\times10^{11}$ CFU/animal/day.

In a preferred embodiment, the method comprises administering to a mono-gastric animal one or more bacterial strains described herein, wherein the bacterial count of each *Bacillus* spore is between $1\times10^5$ and $1\times10^5$ CFU/animal/day, preferably between $1\times10^7$ and $1\times10^{13}$ CFU/animal/day, and more preferably between $1\times10^8$ and $1\times10^{12}$ CFU/animal/day.

The invention relates in a further embodiment to use of the animal feed composition to improve one or more performance parameters in an animal, wherein the performance parameters are selected from the list consisting of improving the feed conversion ratio, improving the body weight gain, improving the feed efficiency, improving the European Production Efficacy Factor and improving the health.

Preferred embodiments of the invention are described in the set of items herein below (ITEM SET I and ITEM SET II).

Item Set I:

1. A *Bacillus* strain comprising one or more of the features selected from the group consisting of:
   i) a gyrB gene with at least 94.7% sequence identity to SEQ ID NO: 1 or a gyrB gene product with at least 99.4% sequence identity to SEQ ID NO: 2 and/or
   ii) an rpoB gene with at least 96.6% sequence identity to SEQ ID NO: 3 or an rpoB gene product with at least 99.7% sequence identity to SEQ ID NO: 4 and/or
   iii) a gyrA gene with at least 89.5% sequence identity to SEQ ID NO: 7 or a gyrA gene product with at least 97.4% sequence identity to SEQ ID NO: 8 and/or
   iv) a genome with an Average Nucleotide Identity to the genome sequence of DSM 29870 of at least 95%.
2. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4.
3. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) a gyrA gene with at least 89.5% sequence identity to SEQ ID NO: 7 or a gyrA gene product with at least 97.4% sequence identity to SEQ ID NO: 8.
4. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) a genome with an Average Nucleotide Identity to the genome sequence of DSM 29870 of at least 95%.
5. A *Bacillus* strain comprising:
   i) an rpoB gene with at least 96.6% sequence identity to SEQ ID NO: 3 or an rpoB gene product with at least 99.7% sequence identity to SEQ ID NO: 4 and
   ii) a gyrA gene with at least 89.5% sequence identity to SEQ ID NO: 7 or a gyrA gene product with at least 97.4% sequence identity to SEQ ID NO: 8.
6. A *Bacillus* strain comprising:
   i) an rpoB gene with at least 96.6% sequence identity to SEQ ID NO: 3 or an rpoB gene product with at least 99.7% sequence identity to SEQ ID NO: 4 and
   ii) a genome with an Average Nucleotide Identity to the genome sequence of DSM 29870 of at least 95%.
7. A *Bacillus* strain comprising:
   i) a gyrA gene with at least 89.5% sequence identity to SEQ ID NO: 7 or a gyrA gene product with at least 97.4% sequence identity to SEQ ID NO: 8 and
   ii) a genome with an Average Nucleotide Identity to the genome sequence of DSM 29870 of at least 95%.
8. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4 and
   iii) a gyrA gene with at least 89.5% sequence identity to SEQ ID NO: 7 or a gyrA gene product with at least 97.4% sequence identity to SEQ ID NO: 8.
9. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4 and
   iii) a genome with an Average Nucleotide Identity to the genome sequence of DSM 29870 of at least 95%.
10. A *Bacillus* strain comprising:
   i) a gyrB gene with at least 94.7% sequence identity to SEQ ID NO: 1 or a gyrB gene product with at least 99.4% sequence identity to SEQ ID NO: 2 and
   ii) a gyrA gene with at least 89.5% sequence identity to SEQ ID NO: 7 or a gyrA gene product with at least 97.4% sequence identity to SEQ ID NO: 8 and
   iii) a genome with an Average Nucleotide Identity to the genome sequence of DSM 29870 of at least 95%.
11. A *Bacillus* strain comprising:
   i) an rpoB gene with at least 96.6% sequence identity to SEQ ID NO: 3 or an rpoB gene product with at least 99.7% sequence identity to SEQ ID NO: 4 and
   ii) a gyrA gene with at least 89.5% sequence identity to SEQ ID NO: 7 or a gyrA gene product with at least 97.4% sequence identity to SEQ ID NO: 8 and iii) a genome with an Average Nucleotide Identity to the genome sequence of DSM 29870 of at least 95%.

12. The *Bacillus* strain according to item 1, wherein the *Bacillus* strain comprises:
   i) a gyrB gene with at least 94.7% sequence identity to SEQ ID NO: 1 or a gyrB gene product with at least 99.4% sequence identity to SEQ ID NO: 2 and
   ii) an rpoB gene with at least 96.6% sequence identity to SEQ ID NO: 3 or an rpoB gene product with at least 99.7% sequence identity to SEQ ID NO: 4 and
   iii) a gyrA gene with at least 89.5% sequence identity to SEQ ID NO: 7 or a gyrA gene product with at least 97.4% sequence identity to SEQ ID NO: 8 and
   iv) a genome with an Average Nucleotide Identity to the genome sequence of DSM 29870 of at least 95%.
13. The *Bacillus* strain according to any of the previous items, wherein the *Bacillus* strain is non-hemolytic, e.g., as determined in Example 8.
14. The *Bacillus* strain according to any of the previous items, wherein the *Bacillus* strain has antimicrobial activity.
15. The *Bacillus* strain according to any of the previous items, wherein the *Bacillus* strain has antimicrobial activity against *Clostridium perfringens*, e.g., as determined in Example 6.
16. The *Bacillus* strain according to any of the previous items, wherein the *Bacillus* strain has antimicrobial activity against *E. coli*, e.g., as determined in Example 7.
17. The *Bacillus* strain according to any of the previous items, wherein the *Bacillus* strain is sensitive to Vancomycin, Clindamycin, Chloramphenicol, Gentamicin, Kanamycin, Streptomycin, Erythromycin and Tetracyclin, e.g., as determined in Example 9.
18. The *Bacillus* strain according to any of the previous items, wherein the *Bacillus* strain has a high compatibility with monensin such as being compatible with at least 2.3 μg/ml monensin as determined in Example 12 (such as at least 2.4 μg/ml monensin, such as at least 2.5 μg/ml monensin, such as at least 2.6 μg/ml monensin or such as at least 2.7 μg/ml monensin as determined in Example 12).
19. The *Bacillus* strain according to any of the previous items, wherein the *Bacillus* strain has a 16S rDNA with more than 98% sequence identity to SEQ ID NO: 9.
20. The *Bacillus* strain according to any of the previous items, wherein the *Bacillus* strain is a *Bacillus subtilis* strain.
21. The *Bacillus* strain according to any of the previous items, wherein the *Bacillus* strain is the *Bacillus* strain having deposit accession number DSM 29870 or a mutant thereof that has antimicrobial activity against *Clostridium perfringens*.
22. A *Bacillus* having deposit accession number DSM 29870 or a strain having all of the identifying characteristics of *Bacillus* DSM 29870 or a mutant thereof.
23. A composition comprising spores of a *Bacillus* strain according to any of items 1 to 22.
24. The composition according to item 23, wherein the *Bacillus* spores of the composition are present as dried spores.
25. The composition according to any of items 23 to 24 which further comprises a carrier.
26. The composition according to item 25, wherein the carrier comprises one or more of the following compounds: water, glycerol, ethylene glycol, 1,2-propylene glycol or 1,3-propylene glycol, sodium aluminium silicate, sodium chloride, sodium benzoate, potassium sorbate, sodium sulfate, potassium sulfate, magnesium sulfate, sodium thiosulfate, calcium carbonate, sodium citrate, dextrin, maltodextrin, glucose, sucrose, sorbitol, lactose, wheat flour, wheat bran, corn gluten meal, starch, farigel, cassava cores, colloidal amorphous silica, Sipernat 50S, polyethylene glycol 200, polyethylene glycol 400, polyethylene glycol 600, polyethylene glycol 1000, polyethylene glycol 1500, polyethylene glycol 4000, carbopol and cellulose.
27. The composition according to any of items 23 to 26, wherein the composition comprises from $10^5$ to $10^{12}$ CFU/g of isolated *Bacillus* spores.
28. An animal feed or an animal feed additive comprising the composition of any of items 23 to 27.
29. The animal feed or animal feed additive of item 28, wherein at least 70% (such as at least 80% or at least 90%) of the *Bacillus* spores survive gastric stability in a mono-gastric animal such as chickens.
30. The animal feed or animal feed additive of any of items 28 to 29 which further comprises one or more components selected from the list consisting of:
   one or more enzymes;
   one or more additional microbes;
   one or more vitamins;
   one or more minerals;
   one or more amino acids; and one or more other feed ingredients.
31. The animal feed or animal feed additive of any of items 28 to 30, wherein the bacterial count of each *Bacillus* spore is $1\times10^4$ and $1\times10^{18}$ CFU/kg of composition, preferably between $1\times10^6$ and $1\times10^{16}$ CFU/kg of composition, and more preferably between $1\times10^8$ and $1\times10^{14}$ CFU/kg of composition.
32. The animal feed or animal feed additive of any of items 28 to 31, wherein the animal feed composition is a mono-gastric animal feed.
33. The animal feed or animal feed additive of any of items 28 to 32, wherein the animal feed or animal feed additive improves gut health of chickens with infection of *Clostridium perfringens* by having antimicrobial activity against *Clostridium perfringens*.
34. The mono-gastric animal feed according to item 32, wherein the mono-gastric animal is selected from the group consisting of pigs, swine, piglets, sows, poultry, turkeys, ducks, chicken, broilers, layers, chicks, fish and crustaceans.
35. The composition according to any of items 23 to 34 for treatment of necrotic enteritis or treatment of a *Clostridium perfringens* infection.
36. The composition according to item 35 for treatment of mono-gastric animals.
37. A method of treating a *Clostridium perfringens* infection or for treating necrotic enteritis in one or more animals comprising administrating to the one or more animals the composition of any of items 23 to 36 to the animal.
38. Use of the composition according to any of items 23 to 27 or the animal feed or animal feed additive of any of items 28 to 33 to improve one or more performance parameters in an animal, wherein the performance parameters are selected from the list consisting of improving the feed conversion ratio, improving the body weight gain, improving the feed efficiency, improving the European Production Efficacy Factor and improving the health.

39. A biologically pure culture of the *Bacillus* strain according to any of items 1 to 22.
40. An isolated *Bacillus* strain according to any of items 1 to 22.
41. An isolated *Bacillus* strain selected from the group consisting of *Bacillus* strain DSM 29870, a strain having all of the identifying characteristics of *Bacillus* DSM 29870 and a mutant thereof.
42. The isolated *Bacillus* strain according to item 41, wherein the identifying characteristics can one or more (such as all) of the characteristics selected from the group consisting of
i) non-hemolytic, e.g., as determined in Example 8,
ii) antimicrobial activity against *Clostridium perfringens*, e.g., as determined in Example 6,
iii) antimicrobial activity against *E. coli*, e.g., as determined in Example 7,
iv) sensitive to Vancomycin, Clindamycin, Chloramphenicol, Gentamicin, Kanamycin, Streptomycin, Erythromycin and Tetracyclin, e.g., as determined in Example 9, and
v) high compatibility with monensin such as being compatible with at least 2.3 μg/ml monensin as determined in Example 12 (such as at least 2.4 μg/ml monensin, such as at least 2.5 μg/ml monensin, such as at least 2.6 μg/ml monensin or such as at least 2.7 μg/ml monensin as determined in Example 12).
43. The *Bacillus* strain according to any of items 1 to 22, the composition according to any of items 23 to 27 or the animal feed or animal feed additive of any of items 28 to 33 for treatment of a *Clostridium perfringens* infection and/or for treatment of necrotic enteritis in one or more animals.

Item Set II:

1. A *Bacillus* strain comprising one or more of the features selected from the group consisting of:
   i) a gyrB gene with at least 94.7% sequence identity to SEQ ID NO: 1 or a gyrB gene product with at least 99.4% sequence identity to SEQ ID NO: 2;
   ii) an rpoB gene with at least 96.6% sequence identity to SEQ ID NO: 3 or an rpoB gene product with at least 99.7% sequence identity to SEQ ID NO: 4; and
   iii) a genome with an Average Nucleotide Identity to the genome sequence of DSM 29870 of at least 95%.
2. The *Bacillus* strain according to item 1, wherein the *Bacillus* strain is non-hemolytic and/or is compatible with monensin (such as with at least 2.4 μg/ml monensin as determined in Example 12).
3. The *Bacillus* strain according to any of the previous items, wherein the *Bacillus* strain has antimicrobial activity against *Clostridium perfringens* or *E. coli*.
4. The *Bacillus* strain according to any of the previous items, wherein the *Bacillus* strain is sensitive to Vancomycin, Clindamycin, Chloramphenicol, Gentamicin, Kanamycin, Streptomycin, Erythromycin and Tetracyclin.
5. The *Bacillus* strain according to any of the previous items, wherein the *Bacillus* strain has a 16S rDNA with more than 98% sequence identity to SEQ ID NO: 9.
6. The *Bacillus* strain according to any of the previous items, wherein the *Bacillus* strain is a *Bacillus subtilis* strain.
7. A *Bacillus* having deposit accession number DSM 29870 or a strain having all of the identifying characteristics of *Bacillus* DSM 29870 or a mutant thereof.
8. A composition comprising spores of a *Bacillus* strain according to any of items 1 to 7.
9. The composition according to item 8 which further comprises a carrier.
10. The composition according to item 9, wherein the carrier comprises one or more of the following compounds: glycerol, ethylene glycol, 1,2-propylene glycol, 1,3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose.
11. The composition according to any of items 8 to 10, wherein the composition comprises from $10^5$ to $10^{12}$ CFU/g of isolated *Bacillus* spores.
12. The composition according to any of items 8 to 11, wherein the composition is an animal feed or animal feed additive.
13. The composition according to any of items 8 to 11 for treatment of necrotic enteritis or treatment of a *Clostridium perfringens* infection.
14. A method of treating a *Clostridium perfringens* infection or for treating necrotic enteritis in one or more animals comprising administrating the composition according to any of items 8 to 13 to the animals.
15. Use of the composition according to any of items 8 to 13 to improve one or more performance parameters in an animal, wherein the performance parameters are selected from the list consisting of improving the feed conversion ratio, improving the body weight gain, improving the feed efficiency, improving the European Production Efficacy Factor and improving the health.

EXAMPLES

Example 1: Identification, Characterization and Deposit of the Biological Material The following biological material was deposited under the terms of the Budapest Treaty at Leibniz-Institut DSMZ-Deutsche Sammlung von Mikro-organismen und Zellkulturen GmbH, Inhoffenstraße 7 B, 38124 Braunschweig Germany, and given the following accession number:

TABLE 1.1

| Deposit of Biological Material | | |
|---|---|---|
| Identification | Accession Number | Date of Deposit |
| *Bacillus subtilis* | DSM 29870 | Jan. 12, 2015 |

*Bacillus subtilis* DSM 29870 was isolated by Novozymes (Novo Nordisk) from an environmental sample collected at Jamaica in 1990. The strain was identified as *Bacillus subtilis* based on 16S rDNA sequencing.

The strain has been deposited under conditions that assure that access to the culture will be available during the pendency of this patent application to one determined by foreign patent laws to be entitled thereto. The deposits represent a substantially pure culture of the deposited strain. The deposits are available as required by foreign patent laws in countries wherein counterparts of the subject application or its progeny are filed. However, it should be understood that the availability of a deposit does not constitute a license to practice the subject invention in derogation of patent rights granted by governmental action.

Sequencing of 16S rDNA Gene

DNA was extracted from a culture of DSM 29870 using QiaAmp DNA Blood Mini Kit (Qiagen art 51106). The kit was used as recommended for extraction of DNA from gram positive bacteria.

16S rDNA was amplified in a total volume of 50 μl by mixing: 10 pmol of each of Primer 16S-F and 16S-R (Table 1.2), 0.2 mM of each nucleotide, 2.5 units Ampli taq, 1×Ampli taq buffer and 5 μl DNA template.

The following PCR program: 94° C. min 2 min (94° C. 30 s, 52° C. 30 s, 72° C. 1 min)×35, 72° C. 10 min was applied on a Perkin Elmer PCR machine. PCR product was sequenced using primer 794-R, 357-F, 1390-R and 1000-F (Table 1.2) on an ABI Prism sequencer.

TABLE 1.2

Primers:

| Primer | Sequence[1] | SEQ ID NO: |
|---|---|---|
| 16S-F | 5'-GAGTTTGATCCTGGCTCAG-3' | SEQ ID NO: 10 |
| 16S-R | 5'-AGAAAGGAGGTGATCCAGCC-3' | SEQ ID NO: 11 |
| 794-R | 5'-ATCTAATCCTGTTTGCTCCCC-3' | SEQ ID NO: 12 |
| 357-F | 5'-TACGGGAGGCAGCAG-3' | SEQ ID NO: 13 |
| 1390-R | 5'-CGGTGTGTRCAAGGCCC-3' | SEQ ID NO: 14 |
| 1000-F | 5'-CAACGAGCGCAACCCT-3' | SEQ ID NO: 15 |

[1]Degeneration of primer: R is A or G.

The 16 S rDNA sequence is shown in SEQ ID NO: 9, the sequence was analysed by BLAST against EMBL database and showed identity to 16 S rDNA sequences of *Bacillus subtilis.*

Example 2: Whole Genome Sequencing and Taxonomic Placement of *Bacillus* Strain DSM 29870

Summary

Average nuclear identity (ANI) and phylogenetics, reveal that the *Bacillus* strain DSM 29870 is a novel subspecies of *Bacillus subtilis.*

Materials and Methods:

Genome Sequencing of DSM 29870

DNA was extracted from a culture of DSM 29870 using QiaAmp DNA Blood Mini Kit (Qiagen art 51106). The kit was used as recommended for extraction of DNA from gram positive bacteria. Genomic DNA was fragmented using a Covaris M220™ ultrasonicator (Covaris, Inc., Woburn, MA) and was used to generate TruSeq™ library ((Illumina, Inc., San Diego, CA) using the Apollo 324™ library prep system (Wafergen Biosystems, Inc., Fremont, CA). The prepared libraries were sequenced using a MiSeq desktop sequencer (Illumina, Inc., San Diego, CA) with MiSeq Reagent Kit v3 (600 cycles) to generate ~360 bp forward and 240 bp reverse paired end reads. Sequences were trimmed and denovo assembled in CLC Genomics Workbench 7.0.4 (CLC Bio, Aarhus, Denmark) using the respective modules.

The following main trimming parameters were used: Ambiguous trim=Yes, Ambiguous limit=2, Quality trim=Yes, Quality Limit=0.01, Minimum number of nucleotides=50, Save broken pairs=Yes. The following main denovo assembly parameters were used: Mapping mode=Map reads back to contigs, Update contigs=Yes, Automatic bibble size=Yes, Minimum contig length=200, Perform scaffolding=yes, Mismatch cost=2, Insertion cost=3, Deletion cost=3, Length fraction=0.8, Similarity graction=0.95.

Benchmark Genome Sequences:

Complete and draft genomes of the public *Bacillus* strains were downloaded from NCBI genomes on Dec. 29, 2014.

Core Genome Phylogenetics:

Prodigal version 2.6 [Hyatt et al., 2010, Prodigal: prokaryotic gene recognition and translation initiation site identification; *BMC Bioinformatics* 11: 119] was used to determine protein sequences.

PhyloPhlan [Segata et al., 2013, PhyloPhlAn is a new method for improved phylogenetic and taxonomic placement of microbes, *Nat. Commun.* 4: 2304] was used to generate a core genome phylogenetic tree based on phylogenetic signals from 400 most conserved protein sequences.

Figure 3:
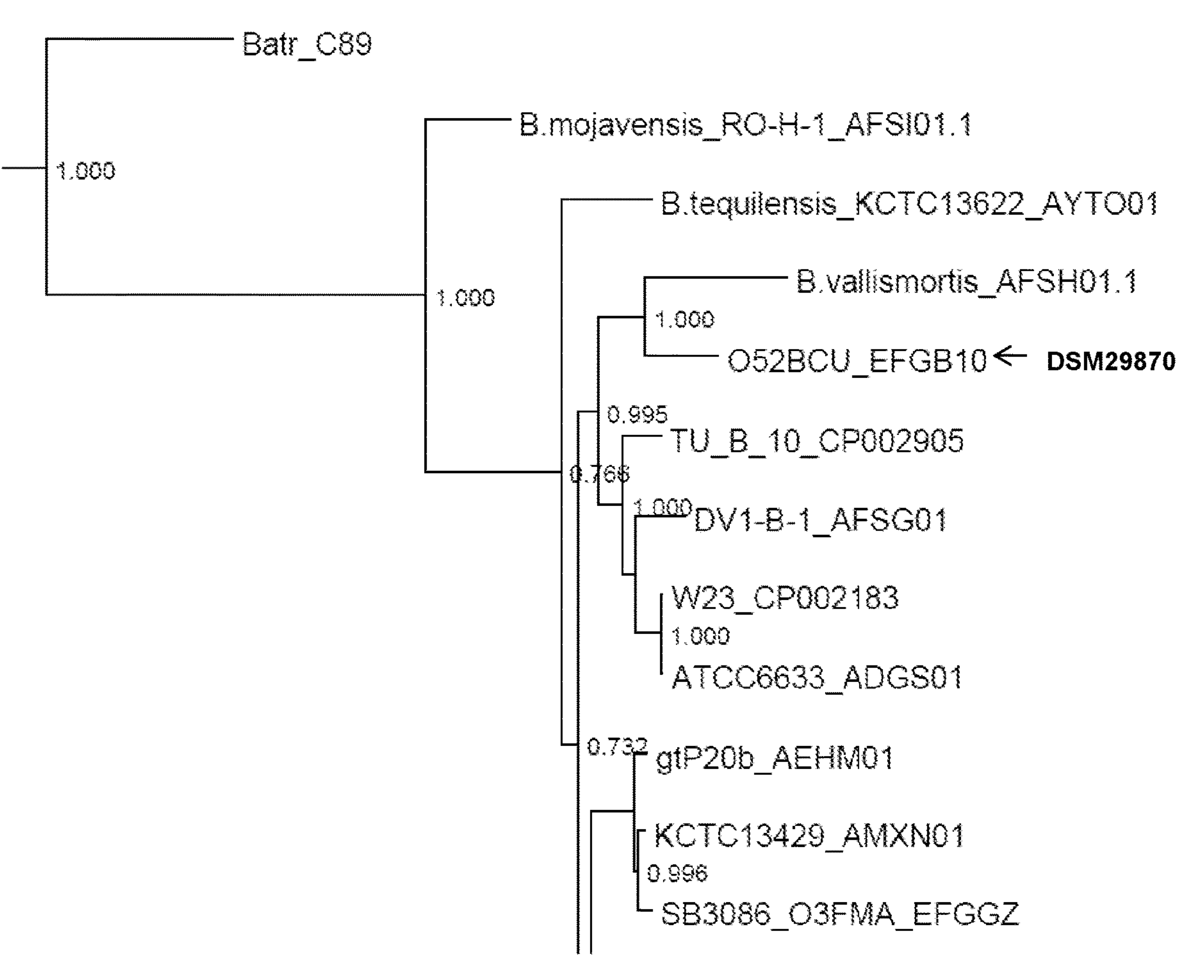
FIG. 3: Rectangular phylogram of members of *Bacillus* genus. This is a zoomed in view of FIG. 2 to show the relationship of O52BCU (alias strain DSM 29870) to its nearest neighbors.

Dendroscope 3 [Huson et al., 2-12. Dendroscope 3: an interactive tool for rooted phylogenetic trees and networks, Syst. Biol. 61: 1061-1067] was used to visualize the tree as a rectangular phylogram with midpoint rooting along with bootstrap support (FIG. 3).

ANI Estimations:

An open source Ruby script (ani.rb) for ANI estimation was obtained from the Kostas lab (enveomics.blogspot.com/2013/10/anirb.html) and used for pair-wise ANI estimations.

Detailed Methods:

All the scripts and programs executed in command line were either run on Ubuntu version 10.04 or version 12.04 (Canonical Ltd.).

Core Genome Phylogenetics:

All the fasta files of the genomes were moved to the same folder and then prodigal version 2.6 was used to determine protein sequences as given in the following example:

Example of Prodigal Script Execution prodigal -i RO_NN-1_CP002906.fasta -a./Protein_files/RO_NN-1_CP002906.faa -c -m All the protein sequences were then moved to a folder in the input folder of the Phylophlan working directory (For example under Protein_files) and then phylophlan was executed as in the following example:

Example of PhyloPhlan Script Execution

./phylophlan.py -nproc 14 -u Protein_files

The newick file generated in output folder was then used as an input for Dendroscope 3 for midpoint rooting and the image was exported in the desired format after the font sizes were adjusted and the desired tree rendering method was selected.

Ani Estimations:

Fasta files of the genomes of each strain were compared pairwise using ani.rb. Example of ani script execution:

ruby ./ani.rb -1 O52BCU_EFGB10.fasta -2 RO_NN-1_CP002906.fasta

The results were output on screen and copied into word document and then summarized as a table.

Results and Discussion:

Ani Estimations:

Average nuclear identity (ANI) is a distance based approach to delineate species based on pair-wise comparisons of genome sequences [Goris et al., 2007, "DNA-DNA hybridization values and their relationship to whole-genome sequence similarities", *Int. J. Syst. Evol. Microbiol.* 57: 81-91]. See the definition of ANI for further details.

Table 2.1 shows pair-wise ANI estimations of Strain DSM 29870 compared to other *Bacillus* species. Data shows that Strain DSM 29870 is most identical (>93%) to *Bacillus subtilis spizezenii* TU-B-10 and *Bacillus vallismortis*. The identity is lower in all other comparisons with species within the *Bacillus* genus. The ANI value is less than 95% in all comparisons and therefore it is difficult to make a definitive statement of taxonomic placement using ANI alone. ANI values less than 95% but higher than 93% are also observed between *Bacillus amyloliquefaciens plantarum* and *amyloliquefaciens* subspecies. Therefore it is quite possible that Strain DSM 29870 is a subspecies of *Bacillus subtilis*.

TABLE 2.1

Two-way pairwise ANI of *Bacillus* strain O52BCU compared to other bacterial genomes (in percentage).

| | *Bacillus subtilis spizezenii* TU-B-10 | *Bacillus vallismortis* | *Bacillus subtilis* 168 | *Bacillus tequilensis* | *Bacillus amyloliquefaciens* YAU_B9601 Y2 | *Bacillus cereus* BMG1.7 | *Bacillus anthracis* ames |
|---|---|---|---|---|---|---|---|
| DSM29870 | 93.68 | 93.84 | 92.12 | 92.07 | 82.76 | 79.95 | 80.59 |

Figure 2A:
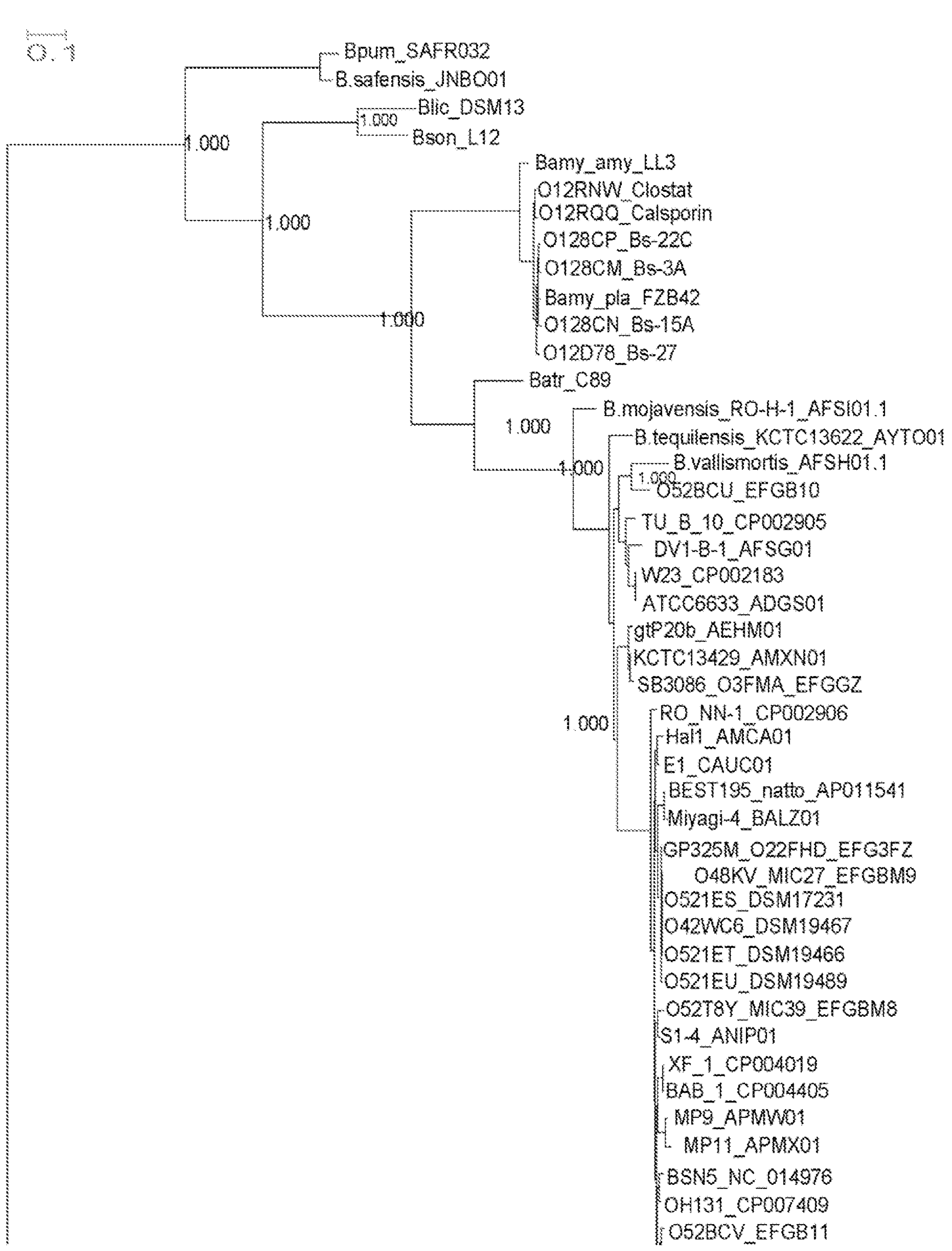
FIGS. 2A and 2B: Rectangular phylogram with midpoint rooting of the members of the *Bacillus* species. All the draft and completed genomes of *Bacillus subtilis* that were available on NCBI on 29-12-2014 were included in the analysis along with representatives from other species. Numbers indicate bootstrap support (1=100%). Scale bar on top left indicates an evolutionary distance of 0.1 amino acid substitutions per position. See the table for species descriptions.
Figure 2B:
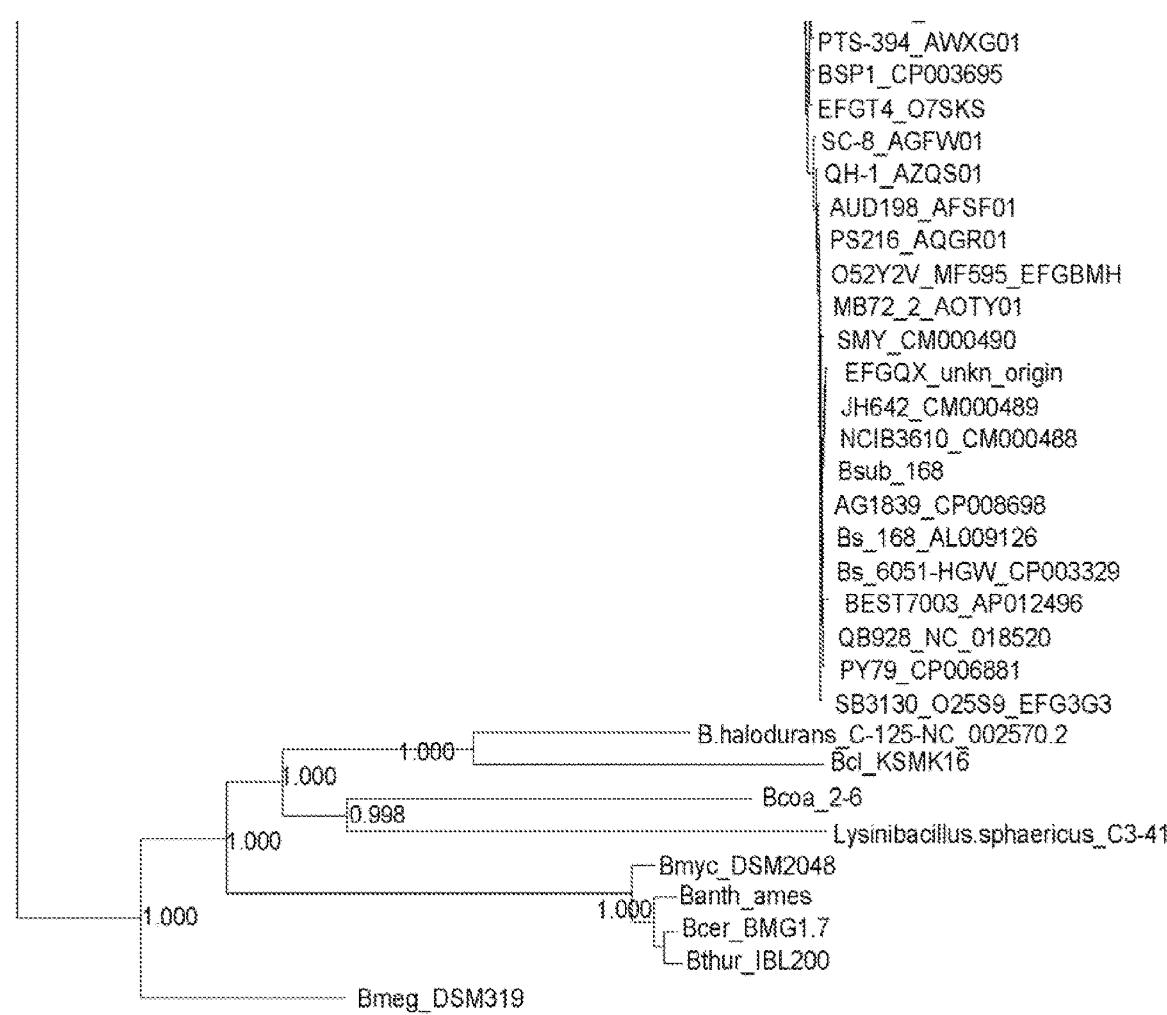

Phylogenetics:

Phylogenetic analysis placed Strain DSM 29870 close to *Bacillus subtilis* subspecies *spizezenii* and *Bacillus vallismortis* (FIG. 3). FIG. 3 is zoomed in to show Strain DSM 29870 relationship to its nearest neighbors. See FIG. 2 for the complete phylogram.

Conclusion:

The Average Nuclear Identity (ANI) value is less than 95% in all comparisons and therefore it is difficult to make a definitive statement of taxonomic placement using ANI alone. However, in combination with phylogenetics, we conclude that the bacterial strain DSM 29870 is distinct to known hitherto known *Bacillus* strains to a level that it at least represents a novel subspecies of *Bacillus subtilis*.

Example 3: GyrB Analysis

Background

Comparative analysis of the gyrB gene encoding the subunit B of the DNA gyrase protein was previously shown to be an efficient tool for taxonomic characterization of members of the *Bacillus subtilis* group. [International Journal of Systematic and Evolutionary Microbiology (2007), 57: 1846-1850].

The gyrB gene sequence of *Bacillus subtilis* strain 168 deposited as CP010052_13 in the EMBL database was used to find the gyrB gene in the genome sequence of DSM 29870.

With a Pearl Script the EMBL:CP010052_13 was used for a BlastN analysis that gave the location—contig number, position and orientation—of the gyrB gene in the genome sequence of DSM 29870. The gyrB gene sequence of DSM 29870 was subsequently manually extracted from the genome sequence.

For the comparative analysis we selected to use only a partial gyrB gene. The partial sequence of the gyrB gene of *Bacillus subtilis* DSM 29870 is shown in SEQ ID NO: 1. The sequence was translated into amino acid sequence (SEQ ID NO: 2). The amino acid sequence of the partial gyrB gene product cover amino acids 49-614 of the gyrB gene product in *Bacillus subtilis* type strain UNIPROT:P05652 [Moriya et al., 1985, "Structure and function of the region of the replication origin of the *Bacillus subtilis* chromosome. III. Nucleotide sequence of some 10,000 base pairs in the origin region." *Nucleic Acids Res.* 13: 2251-2265].

The Amino acid and DNA sequences were analyzed by BLAST [Altschul et al., 1990, "Basic local alignment search tool", J. Mol. Biol. 215: 403-410]. The amino acid sequence showed 99.3% identity to the closest related strain of *Bacillus subtilis*, the DNA sequence showed 94.6% identity to the closest relative, *Bacillus subtilis* subsp. *Spizizenii*. This indicates that *Bacillus subtilis* DSM 29870 is a novel subspecies of *Bacillus subtilis.*

Example 4: rpoB Analysis

Background

The rpoB gene encoding the RNA polymers beta subunit was previously used as a phylogenetic marker. The extensive use of rpoB was reviewed [Adékambi et al., 2009, "The rpoB gene as a tool for clinical microbiologists", *Trends in Microbiology* 17(1): 37-45]. It was used to discriminate sub-groups/closely related *Bacillus* species [Qi et al., 2001, "Utilization of the rpoB Gene as a Specific Chromosomal Marker for Real-Time PCR Detection of *Bacillus anthracis", Appl. Environ. Microbiol.* 67(8): 3720-3727].

The rpoB gene sequence of *Bacillus subtilis* wild type Marburg strain deposited in the EMBL database under L24376 [Boor et al., 1995, "Genetic and transcriptional organization of the region encoding the beta subunit of *Bacillus subtilis* RNA polymerase", *J. Biol. Chem.* 270(35): 20329-20336] was used to find the rpoB gene in the genome sequence of DSM 29870.

With a Pearl Script the EMBL:L24376 was used for a BlastN analysis that gave the location—contig number, position and orientation—of the rpoB gene of DSM 29870. The rpoB gene sequence of DSM 29870 was manually extracted from the genome sequence. For the comparative analysis we selected to use only a partial rpoB gene. The partial sequence of the rpoB gene of *Bacillus subtilis* DSM 29870 is shown in SEQ ID NO: 3.

The sequence was translated into the amino acid sequence. The amino acid sequence of the partial rpoB gene product is shown in SEQ ID NO: 4. It covers the amino acids equivalent to 1 to 1193 of the rpoB gene product in *Bacillus subtilis* of EMBL: L24376 [Boor et al., 1995, "Genetic and transcriptional organization of the region encoding the beta subunit of *Bacillus subtilis* RNA polymerase", *J. Biol. Chem.* 270(35): 20329-20336].

The amino acid and DNA sequences were analyzed by BLAST [Altschul et al., 1990, "Basic local alignment search tool." J. Mol. Biol. 215: 403-410]. The amino acid sequence showed 99.4% identity to the closest related strain of *Bacillus subtilis*, the DNA sequence showed 96.5% identity to the closest relative, *Bacillus subtilis* subsp. *Spizizenii*. This indicates that *Bacillus subtilis* DSM 29870 is a novel subspecies of *Bacillus subtilis.*

Example 5: Comparative Analysis of GyrA Extracted from the Genome Sequence

Background

Partial sequence of the gyrA gene encoding the alpha subunit of the DNA gyrase protein has previously been used as a phylogenetic marker to discriminate members of the *Bacillus subtilis* group. Twelve strains of *Bacillus amyloliquefaciens, Bacillus atrophaeus, Bacillus licheniformis, Bacillus mojavensis, Bacillus subtilis* subsp. *subtilis, Bacillus subtilis* subsp. *spizizenii* and *Bacillus vallismortis* were sequenced, and it was shown that *Bacillus subtilis* subsp. *subtilis* could be discriminated from *Bacillus subtilis* subsp. *spizizenii* based on this gene sequence [Chun & Bae, 2000, "Phylogenetic analysis of *Bacillus subtilis* and related taxa based on partial gyrA gene sequences", Antonie van Leeuwenhoek 78: 123-127,]. The partial gyrA gene sequence of *Bacillus amyloliquefaciens* KCTC $1660^T$ deposited in EMBL as AF272015 was used to identify and extract the gyrA gene from the genome of DSM 29870.

Data Analysis

With a Pearl Script the EMBL:AF272015 was used for a BlastN analysis that gave the location—contig number, position and orientation—of the partial gyrA gene of DSM 29870. The partial gyrA gene sequence of DSM 29870 was manually extracted from the genome sequence.

The partial sequence of the gyrA gene of *Bacillus subtilis* DSM 29870 is shown in SEQ ID NO: 7. The sequence was translated into amino acid sequence. The amino acid sequence of the partial gyrA gene product covers the amino-acids shown in SEQ ID NO: 8. The Amino acid and DNA sequences were analyzed by BLAST [Altschul et al., 1990, "Basic local alignment search tool", *J. Mol. Biol.* 215: 403-410]. The amino acid sequence show 97.3% identity to the closest related strain of *Bacillus subtilis* subsp *spizizenii* TU-B10, the DNA sequence showed 89.4% identity to the closest relative, *Bacillus subtilis* subsp. *spizizenii* ATCC6633, this indicates that *Bacillus subtilis* DSM 29870 is a novel subspecies of *Bacillus subtilis.*

Example 6: Determination of Inhibition of Growth of *Clostridium perfringens*

*Clostridium perfringens* strains, 23 and 48 (both are netB positive) [Gholamiandekhordi et al., 2006, "Molecular and phenotypical characterization of *Clostridium perfringens* isolates from poultry flocks with different diseasestatus", Vet. Microbiol. 113: 143-152] were grown overnight in tryptic soy broth (BD part 211822) supplemented with 0.6% yeast extract (BD part 212750) at 35° C. under static anaerobic conditions. 250 μL of the overnight culture of *Clostridium perfringens* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar. Plates were stored in absence of oxygen until use.

*Bacillus* DSM 29870 was grown overnight in tryptic soy broth at 35° C. under aerobic conditions. 1000 μL of the *Bacillus* culture was collected and fractionated into cell-free supernatant and cells by centrifugation. 20 μL of cell-free supernatant or 100× diluted cells in phosphate buffered saline were added directly to the wells in the *Clostridium perfringens* inoculated agar plates. A control well contained 20 μL of phosphate buffer saline. The plates were incubated for 18 hours at 35° C. under anaerobic conditions.

Inhibition of the *Clostridium perfringens* strain was noted by a circular clearing zone around the well of interest. The phosphate buffer saline well was considered a negative control based on lack of clearing zone around the well.

Cell-free supernatant and 100× diluted cells of *Bacillus* strain DSM 29870 was able to consistently inhibit growth of *C. perfringens* strains 23 and 48 in vitro. Inhibition was also seen by competitor strain "CloSTAT", for both supernatant and cells, but was not seen with competitor strain GalliproTect. "CloSTAT" is a strain of *Bacillus amyloliquefaciens* that was isolated from the commercial DFM product CloSTAT, Kemin. "GalliproTect" is a strain of *Bacillus licheniformis* that was isolated from the commercial product Gallipro Tect, Chr. Hansen.

Example 7: Determination of Inhibition of Growth of *Escherichia coli*

*Escherichia coli* strains, ATCC10536 or ATCC25922, were grown overnight in tryptic soy broth (BD part 211822) supplemented with 0.6% yeast extract (BD part 212750) at 35° C. under static anaerobic conditions. 100 μL of the overnight culture of *Escherichia coli* was added to 250 mL of tryptic soy agar supplemented with 0.6% yeast extract at 40° C. and poured into rectangular petri plates (Nunc part 267060). The inoculated agar was then allowed to cool at room temperature after which an 8 mm diameter well was made in the agar.

*Bacillus* DSM 29870 was grown overnight in tryptic soy broth at 35° C. under aerobic conditions. 1000 μL of the *Bacillus* culture was collected and fractionated into cell-free supernatant and cells by centrifugation. 20 μL of cell-free supernatant or 100× diluted cells in phosphate buffer saline were added directly to the wells in the *Escherichia coli* inoculated agar plates. A control well contained 20 μL of phosphate buffer saline. The plates were incubated for 18 hours at 30° C. under aerobic conditions.

Inhibition of the *Escherichia coli* strain was noted by a circular clearing zone around the well of interest. The phosphate buffer saline well was considered a negative control based on lack of clearing zone around the well.

Cell-free supernatant and 100× diluted cells of *Bacillus* strains DSM 29870 was able to consistently inhibit growth of *E. coli* strains ATCC10535 and ATCC25922 in vitro. Inhibition was also seen by competitor strain CloSTAT, for both supernatant and cells.

Example 8: Non-Hemolytic

Hemolysis was tested according to the Technical Guidance on the assessment of the toxigenic potential of *Bacillus* species used in animal nutrition, EFSA Journal 2011; 9(11): 2445.

Sheep blood agar plates were purchased as ready to use (Becton Dickenson art 254053 or 254087). Alternatively, the agar plates can be prepared by adding 5% defibrinated sheep blood (obtained from Statens Serum Institute, Denmark) to TS-agar (Oxoid CM 131). Agar should be autoclaved at 121° C. for 20 minutes and cooled down to about 40° C. before adding the blood immediately before pouring the plates.

The *Bacillus* strains were taken from the preservation at −80° C. and streaked on TSA agar plates, which were incubated at 30° C. overnight or until growth appeared. From a single colony as little as possible of the material was used to streak a line on ¼ of an agar plate. The plate was incubated at 30° C. for 72 hours. Hemolysis/clearing zones of the *Bacillus* strains to be tested were compared with the positive and negative control. As positive control *Bacillus subtilis* ATCC 21332 was used. As negative control *Bacillus subtilis* 168 was used.

In a screening of 599 independent isolates of *Bacillus* 223 strains (37%) were hemolysis negative. In another screening 21 of 65 independent isolates of *Bacillus* (32%) were hemolysis negative. Both screenings exclusively comprised strains that based on identification by 16S rDNA sequencing belong to *Bacillus subtilis, Bacillus licheniformis, Bacillus pumilus* and *Bacillus amyloliquefaciens* (or *Bacillus* species that are difficult to discriminate from these species based on 16 S rDNA sequencing).

The non-Hemolytic *Bacillus* strains therefore seem to be common and fairly abundant in nature, but only comprising a minority of the natural strains. The non-hemolytic strains seem to be more abundant in *Bacillus licheniformis*, while most *Bacillus amyloliquefaciens* strains appear hemolytic. The following strain from this screening was hemolysis negative and selected for further studies: *Bacillus* DSM 29870.

Example 9: Sensitivity to Antibiotics

The minimal inhibitory concentrations (MIC) of eight antibiotics against *Bacillus* strains DSM 29870 were determined using broth micro dilution essentially as described in the CLSI guidelines (M07-A9 Methods for Dilution Antimicrobial Susceptibility Tests for Bacteria That Grow Aerobically; 2012). Only modification was that volumes were changed; 90 μl MHB with bacteria was added to 10 μl antibiotics dilutions, cfu's of bacteria and concentration of antibiotics were changed so final concentrations and final cfu's matched the guideline. The plates were incubated for 20-24 h instead of 16-20 h. The control strain recommended in the CLSI standard *Staphylococcus aureus* ATCC 29213 was used as control strain.

Materials

Strains:

*Bacillus subtilis* DSM 29870

*S. aureus* ATCC 29213

Antibiotics:

Chloramphenicol (Sigma C1919, 10 mg/ml, solubilized in 96% ethanol)

Clindamycin (Sigma PHR1159, 10 mg/ml, solubilized in water)

Erythromycin (ABBOTICIN from Amdipharm 40501, 50 mg/ml, solubilized in 96% ethanol)

Gentamycin (Biomedicals inc., 190057, 10 mg/ml, solubilized in water)

Kanamycin (Sigma, CAS no. 25389-94-0, 50 mg/ml, solubilized in water)

Streptomycin (Sigma, S1277, 10 mg/ml, solubilized in water)

Tetracycline (Sigma, T3383, 10 mg/ml, solubilized in water)

Vancomycin (Sigma, V-8138, 10 mg/ml, solubilized in water)

Mueller Hinton Broth 2 (Sigma/Fluka 90922)

0.9% NaCl (Sigma/RdH 31434/Merck 106404)

Tryptone soya agar plates (Oxoid CM 131)

Microtiter plates: Costar plate, polypropylene, round bottom, Corning 3879

Method

Preparation of Bacteria:

A few colonies of *Bacillus* spp. (<1 day old) were inoculated into Mueller Hinton Broth 2 (MHB) and incubated for around 4 hours at 37° C. $OD_{600}$ (BioPhotometer plus, Eppendorf) was measured and adjusted to 0.25 (equivalent to McFarland 0.5) in MHB. For the control strain direct colony suspension was used. A few colonies of *S. aureus* ATCC 29213 (<1 day old) were suspended in MHB and $OD_{600}$ (BioPhotometer plus, Eppendorf) was measured and adjusted to 0.10-0.12 (equivalent to McFarland 0.5) in MHB. The bacterial suspensions were diluted 200× in MHB.

Preparation of Assay Plates:

Antibiotics were diluted to the concentration of 640 μg/ml in MHB. A two fold dilution series was prepared in MHB down to the concentration 0.625 μg/ml. 10 μl of each dilution and of each antibiotic was pipetted into a microtiter plates. Later, when the antibiotics were mixed with the suspension of bacteria, the samples were diluted 10× (10 μL sample in a total volume of 100 μl). This resulted in the final test range of 0.06-64 μg/ml.

If the plates were not used right away the plates are stored in the freezer at −20° C. until usage.

90 μl of the bacterial suspensions were added to the assay plates. The assay plates were incubated in a plastic bag with at wet cloth at 37° C. for 20-24 h. The MIC was determined as the lowest concentration of antibiotic that completely inhibited growth of bacteria as detected by the unaided eye.

Cfu Estimation:

A 10-fold dilution series in 0.9% NaCl was made to the 10-3 of the cultures inoculated into the microtiter plates. 2×100 ul from the 10-3 dilution were plated onto two TSA plates. The plates were incubated overnight at 37° C. Number of CFU/ml was counted.

Three biological replicates of the assay were performed for *Bacillus* DSM 29870.

Results:

The MIC values obtained for *B. subtilis* DSM 29870 showed that the breakpoint values were equal to or below the breakpoint values given in the EFSA guideline (EFSA Journal 2012; 10(6):2740).

As a control *S. aureus* ATCC 29213 was tested in parallel and had MIC values within the ranges given by the CLSI standard (M100-S24 Performance Standards for Antimicrobial Susceptibility Testing; informational Supplement, 2014).

The amount of bacteria inoculated into the assay plates was measured (CFU/ml). In general the CFU/ml was very close to the target value of $1.5*10^5$ CFU/ml. However, the CFU/ml for the *Bacillus* strains was most possibly higher than the actual value, since the bacteria tend to aggregate and one aggregated will only result in one colony forming unit (Tables 9.1 and 9.2).

TABLE 9.1

MIC results for *B. subtilis* DSM 29870

| Antibiotic | MIC 1 μg/ml | MIC 2 μg/ml | MIC 3 μg/ml | EFSA* breakpoints μg/ml |
|---|---|---|---|---|
| Chloramphenicol | 4 | 8 | 4 | 8 |
| Clindamycin | 0.25 | 0.25 | 0.25 | 4 |
| Erythromycin | 0.125 | 0.125 | 0.125 | 4 |
| Gentamycin | 0.25 | 0.125 | 0.25 | 4 |
| Kanamycin | 2 | 1 | 2 | 8 |
| Streptomycin | 4 | 4 | 8 | 8 |

TABLE 9.1-continued

| MIC results for *B. subtilis* DSM 29870 | | | | |
|---|---|---|---|---|
| Antibiotic | MIC 1 µg/ml | MIC 2 µg/ml | MIC 3 µg/ml | EFSA* breakpoints µg/ml |
| Tetracycline | 0.25 | 0.25 | 0.25 | 8 |
| Vancomycin | 0.25 | 0.25 | 0.25 | 4 |
| CFU/ml | 4.2*10^5 | 2.1*10^5 | 1.4*10^5 | |

*EFSA Journal 2012; 10(6): 2740

TABLE 9.2

| MIC results for *S. aureus* ATCC 29213 | | | | |
|---|---|---|---|---|
| Antibiotic | MIC 1 µg/ml | MIC 2 µg/ml | MIC 3 µg/ml | CLSI* breakpoints µg/ml |
| Chloramphenicol | 8-16 | 16 | 8 | 2-16 |
| Clindamycin | 0.125 | 0.25 | 0.125 | 0.06-0.25 |
| Erythromycin | 0.5 | 0.5 | 0.5 | 0.25-1 |
| Gentamycin | 0.5 | 0.5 | 0.5 | 0.12-1 |
| Kanamycin | 4 | 4 | 4 | 1-4 |
| Streptomycin | 8 | 8 | 8 | No information |
| Tetracycline | 0.5 | 1 | 1 | 0.12-1 |
| Vancomycin | 0.5 | 1 | 1 | 0.5-2 |
| CFU/ml | 5.2*10^5 | 7.0*10^5 | 7.0*10^5 | |

*M100-S24 Performance Standards for Antimicrobial Susceptibility Testing; informational Supplement, 2014

Example 10 gyrB Analysis

PCR Amplification of gyrB

For the PCR amplification 1 µL of genomic DNA (see Example 2) was mixed with 12.5 µL Reddymix Extensor PCR solution (Thermo Fisher Scientific, Surrey, UK), 1 µL of each of 10 µM solutions of primers 3AF and 4R2 (Table 10.1) and 9.5 µl distilled water. For negative control PCR reactions 1 µL MQ water was added instead of DNA.

TABLE 10.1

| Primers: | | |
|---|---|---|
| Primer | Sequence[1] | SEQ ID NO: |
| 3AF | 5'-GTMTGGGAAATTGTSGACAA-3', | SEQ ID NO: 16 |
| 4R2 | 5'-GCGGTTCYACTTTRTCRCCC-3' | SEQ ID NO: 17 |

[1]Degeneration of primers: M is A or C, S is G or C, Y is C or T and R is A or G.

The PCR thermal cycler (DNA Engine DYAD BIORAD) was programmed to run; 92° C. for 2 min, 40*[94° C. for 30 s, 52° C. for 30 s, 72° C. for 60 s], 72° C. for 10 min. The PCR product was evaluated by agarose gel electrophoresis on FlashGel cassette (Lonza, Rockland, ME USA), using FlashGel DNA marker 100 bp-4000 bp, to estimate size of the amplicon. The PCR amplification of gyrB gene was successful when a band of about 1700 nt was seen on the gel.

Purification of PCR Products

The PCR purification was done with Multiscreen PCR 96 well filterplate (Millipore, Ireland); The entire volume of the PCR reaction was taken to one well in a 96 well plate, MilliQ water up to 100 µL was added. The plate was subjected to vacuum until it was dry (20-25 s) 100 µL milli water was added, the vacuum step was repeated. The PCR product was eluted by addition of 50 µL elution buffer (elution buffer was water) and pipetting the PCR product away from the top of the filter. The purified PCR product was stored at −22° C.

Sequencing of the Genes

The DNA concentration of the purified PCR product was quantified on NanoDrop 1000 Spectrophotometer (Thermo Fisher, Waltham, MA, USA). Four sequence reactions were set up each using 10 ng PCR product, 1 uL primer of 10 mM of one of the primers C-F, D-R, BS-F or BS-R (Table 10.2) and distilled water to 12 µL. The solutions were mixed and used for Sanger sequencing on an ABI Prism sequencer [Sanger,»DNA sequencing with chain-terminating inhibitors, «*Proceedings of the National Academy of Sciences of the United States of America*, p. 5463-5467, December 1977].

TABLE 10.2

| Primers: | | |
|---|---|---|
| Primer | Sequence[1] | SEQ ID NO: |
| C-F | 5'-GGYATYCCIGTCGGCATYCA-3' | SEQ ID NO: 18 |
| D-R | 5'-TCCATSGTYGTYTCCCAMAG-3' | SEQ ID NO: 19 |
| BS-F | 5'-GAAGGCGGNACNCAYGAAG-3' | SEQ ID NO: 30 |
| BS-R | 5'CTTCRTGNGTNCCGCCTTC-3' | SEQ ID NO: 31 |

[1]Degenerations of primers: Y is C or T, I is inosine, S is G or C and M is A or C, N is A, C, G or T.

The sequence traces were assembled to a partial gyrB gene using the SeqMan program of the Lasergene (DNA STAR 7, Lasergene). The sequence of the entire PCR product minus the primer region of *Bacillus subtilis* DSM 29870 is shown in SEQ ID NO 32. The sequence was translated into amino acid sequence (SEQ ID NO: 33). The amino acid sequence of the partial gyrB gene product cover amino acids 49-614 of the gyrB gene product in *Bacillus subtilis* type strain UNIPROT:P05652 [Moriya et al., 1985, "Structure and function of the region of the replication origin of the *Bacillus subtilis* chromosome. Ill. Nucleotide sequence of some 10,000 base pairs in the origin region", *Nucleic Acids Res.* 13: 2251-2265]. The Amino acid and DNA sequences were analyzed by BLAST [Altschul et al., 1990, "Basic local alignment search tool", *J. Mol. Biol.* 215: 403-410]. The amino acid sequence showed 99.2% identity to the two closest related sequences which were from *Bacillus subtilis* subsp. *spizizenii* strains ATCC663 and W23, respectively. The DNA sequence showed 94.7% identity to the closest related sequence which was from *Bacillus subtilis* subsp. *spizizenii* TU-B-10, this indicates that *Bacillus subtilis* DSM 29870 is a novel subspecies of *Bacillus subtilis.*

Example 11 rpoB Analysis

Background

The rpoB gene encoding the RNA polymers beta subunit was previously used as a phylogenetic marker to discriminate sub-groups/closely related species in *Bacillus* [Qi et al., 2001, "Utilization of the rpoB Gene as a Specific Chromosomal Marker for Real-Time PCR Detection of *Bacillus anthracis*", Appl. Environ. Microbiol. 67(8): 3720-3727]. By comparison of rpoB genes from *Bacillus amyloliquefaciens* and *Bacillus subtilis* primers were designed and a similar sequenced based evaluation was used to show that DSM 29870 is a novel subspecies of *Bacillus subtilis.*

PCR Amplification of rpoB

For the PCR amplification 1 µL of genomic DNA (see Example 2) was mixed with 12.5 µl Reddymix Extensor PCR solution (Thermo Fisher Scientific, Surrey, UK), 1 μL of each of 10 μM solutions of primers rpoB-PCR-F and rpoB-PCR-R (Table 11.1) and 9.5 μl distilled water. For negative control PCR reactions 1 μL MQ water was added instead of DNA.

TABLE 11.1

| Primers: | | |
|---|---|---|
| Primer | Sequence | SEQ ID NO: |
| rpoB-PCR-F | 5'-TACGCATGATTTGAGGGGTG-3' | SEQ ID NO: 20 |
| rpoB-PCR-R | 5'-AACCGATGTCACTTGCCTTTA-3' | SEQ ID NO: 21 |

The PCR thermal cycler (DNA Engine DYAD BIORAD) was programmed to run; 92° C. for 2 min, 40*[94° C. for 30 s, 52° C. for 30 s, 72° C. for 60 s], 72° C. for 10 min. The PCR product was evaluated by agarose gel electrophoresis on FlashGel cassette (Lonza, Rockland, ME USA), using FlashGel DNA marker 100-4000 bp, to estimate size of the amplicon. The PCR amplification of rpoB gene was successful when a band of about 3600 nt was seen on the gel (theoretical size is 3639 nt based on embl:L24376).

Purification of PCR Products

The PCR purification was done with Multiscreen PCR 96 well filterplate (Millipore, Ireland); The entire volume of the PCR reaction was taken to one well in a 96 well plate, MilliQ water up to 100 μL was added. The plate was subjected to vacuum until it was dry (20-25 s) 100 μL milli water was added, the vacuum step was repeated. The PCR product was eluted by addition of 50 μL elution buffer (elution buffer was water) and pipetting the PCR product away from the top of the filter. The purified PCR product was stored at −22° C.

Sequencing of the Genes

The DNA concentration of the purified PCR product was quantified on NanoDrop 1000 Spectrophotometer (Thermo Fisher, Waltham, MA, USA). Eight sequence reactions were set up each using 10 ng PCR product, 1 uL primer of 10 mM of one of the primers rpoB-seq-F1, rpoB-seq-F2, rpoB-seq-F3, rpoB-seq-F4, rpoB-seq-R1, rpoB-seq-R2, rpoB-seq-R3, and rpoB-seq-R4 and distilled water to 12 μL. The solutions were mixed and used for Sanger sequencing on an ABI Prism sequencer.

TABLE 11.2

| Primers: | | |
|---|---|---|
| Primer | Sequence | SEQ ID NO: |
| rpoB-seq-F1 | 5'-TTAATTAACAAAGAAACTGG-3' | SEQ ID NO: 22 |
| rpoB-seq-F2 | 5'-ATGTAATCGGCAATGCTTAC-3' | SEQ ID NO: 23 |
| rpoB-seq-F3 | 5'-AGGCTGTGCCTTTGATGCAG-3' | SEQ ID NO: 24 |
| rpoB-seq-F4 | 5'-GAAACGTAAGATTTCTGAAG-3' | SEQ ID NO: 25 |
| rpoB-seq-R1 | 5'-GAGAGCACGCAAAAGAACCG-3' | SEQ ID NO: 26 |
| rpoB-seq-R2 | 5'-GTTTCAATCGGACACATACG-3' | SEQ ID NO: 27 |

TABLE 11.2-continued

| Primers: | | |
|---|---|---|
| Primer | Sequence | SEQ ID NO: |
| rpoB-seq-R3 | 5'-CCGTCAGCAAGGATTTCTCC-3' | SEQ ID NO: 28 |
| rpoB-seq-R4 | 5'-TCCATACCTAAGCTTTGAAG-3' | SEQ ID NO: 29 |

The sequence traces were assembled to a partial rpoB gene using the SeqMan program of the Laser Gene (DNA STAR 7, lasergene) the sequence of the entire PCR product minus the primer region of *Bacillus subtilis* DSM 29870 is shown in SEQ ID NO: 34. The sequence was translated into amino acid sequence (SEQ ID NO:35). The amino acid sequence of the partial gyrB gene product cover amino acids 49-614 of the rpoB gene product in *Bacillus subtilis* type strain UNIPROT:P05652 [Moriya et al., 1985, "Structure and function of the region of the replication origin of the *Bacillus subtilis* chromosome. Ill. Nucleotide sequence of some 10,000 base pairs in the origin region", *Nucleic Acids Res.* 13: 2251-2265]. The amino acid and DNA sequences were analyzed by BLAST [Altschul et al., 1990, "Basic local alignment search tool", *J. Mol. Biol.* 215: 403-410. The amino acid sequence showed 99.3% identity to the 3 closest related sequences of *Bacillus subtilis* subsp. *spizizenii* (strain ATCC 23059, NRRL B-14472, W23) and ATCC6633 and a third that was poorly annotated in UniProt database. The DNA sequence showed 96.5 identity to the closest related sequence which was from *Bacillus subtilis* subsp. *spizizenii* TU-B-10. This indicates that *Bacillus subtilis* DSM29870 is a novel subspecies of *Bacillus subtilis*.

Example 12: Determination of Monensin Compatibility

Monensin compatibility of DSM 29870 was determined using a modified broth micro dilution similar to the method described in the Example 9. Briefly, a single colony of *Bacillus* spp. (from overnight tryptic soy agar plates) was inoculated into Mueller Hinton Broth (MHB) and cultured overnight. Sterile media was then inoculated with the overnight culture and allowed to grow for 4 hours to test bacteria in log growth phase. Cultures were then diluted once more 1:200 into fresh MHB and 90 μL of this inoculated broth was added to the diluted monensin at the indicated concentrations. Prior art strains were also tested for comparison: NN019785, NN062266 (NRRL B-50013), NN062267 (NRRL B-50104), NN062278 (PTA-6507), NN062319 (FERM BP-1096), NN062440, NN062441 (DSM 17236), NN062439.

Strains:

*Bacillus subtilis* DSM 29870.
*Bacillus licheniformis* NN019785.
*Bacillus amyloliquefaciens* NN062266 (NRRL B-50013).
*Bacillus subtilis* NN062267 (NRRL B-50104).
*Bacillus subtilis* NN062278 (PTA-6507).
*Bacillus amyloliquefaciens* NN062319 (FERM BP-1096).
*Bacillus subtilis* NN062440.
*Bacillus licheniformis* NN062441 (DSM 17236).
*Bacillus amyloliquefaciens* NN062439.

Materials:

Monensin sodium salt (Sigma, CAS no. 22373-78-0, solubilized in 96% ethanol).

Mueller Hinton Broth (Becton, Dickinson and Company, 275730).

Tryptic soy agar (Becton, Dickinson and Company, 236920).

Micro titer plates: Costar plate, polypropylene, flat bottom, Corning, 3628.

Borosilicate glass tubes: Kimbale, 16×125 mm, 73500-16125.

Adhesive gas permeable seals: Thermo Scientific, AB-0718.

Preparation of Bacteria:

*Bacillus* spp. were grown overnight on tryptic soy agar plates (40 g/L) at 37° C. Mueller Hinton broth (21 g/L) was dissolved in water and autoclaved in glass tubes containing 5 mL of broth each. A single colony of *Bacillus* spp. (from overnight plates) was inoculated into Mueller Hinton Broth (MHB) and incubated overnight at 37° C. shaking at 200 rpm. A 5 mL glass tube of fresh, sterile media was then inoculated with 25 mL of overnight culture and allowed to grow for 4 hours at 37° C. Cultures were then diluted once more 1:200 into fresh MHB. 90 μL of this inoculated broth was then added to the diluted antibiotic at the indicated concentrations.

Preparation of Assay Plates:

Monensin was diluted into 96% ethanol to a concentration of 800 μg/mL. This solution was then diluted 10-fold into sterile phosphate buffer to a concentration of 80 μg/mL. A two fold dilution series was prepared in MHB down to the concentration 2.5 μg/mL. 10 μl of each dilution and of each antibiotic was pipetted into a microtiter plate. Later, when the antibiotics were mixed with the suspension of bacteria, the samples were diluted 10× (10 μL sample in a total volume of 100 μl). This resulted in the final test range of 0.25-8 μg/ml.

90 μl of the bacterial suspensions were added to the assay plates. The assay plates were then covered with an adhesive glass permeable seal and incubated overnight at 37° C. shaking at 200 rpm. The maximum compatible concentration was determined similar to a MIC analysis as the concentration above that which inhibited 80% of bacteria as detected by the unaided eye.

Results:

A potential challenge of delivering *Bacillus* spp. in feed is the common use of antibiotics as growth promoters in feed. Therefore it is necessary to determine the compatibility of strains with commonly-used feed antibiotics in order to identify any potential conflicts with use as a direct fed microbial. Therefore, the monensin compatibility DSM 29870 was determined along with prior art strains. DSM 29870 has a higher level of compatibility with monensin than the prior art strains included herein: NN019785, NN062266 (NRRL B-50013), NN062267 (NRRL B-50104), NN062278 (PTA-6507), NN062319 (FERM BP-1096), NN062440, NN062441 (DSM 17236), NN062439.

TABLE 12.1

Monensin compatibility results

| | Deposit number | Species | Product Name | Monensin (μg/mL) |
|---|---|---|---|---|
| NN062677 | DSM29870 | *Bacillus subtilis* | | 2.7 |
| NN019785 | | *Bacillus licheniformis* | BioPlus 2B (Chr. Hansen) | 0.8 |
| NN062266 | NRRL B-50013 | *Bacillus amyloliquefaciens* | Eviva Pro (Dupont) | 1.1 |
| NN062267 | NRRL B-50104 | *Bacillus subtilis* | Eviva Pro (Dupont) | 1.1 |
| NN062278 | PTA-6507 | *Bacillus subtilis* | Eviva Pro (Dupont) | 1.4 |
| NN062319 | FERM BP-1096 | *Bacillus amyloliquefaciens* | Calsporin (Calpis) | 2.2 |
| NN062440 | | *Bacillus subtilis* | GalliPro Max (Chr. Hansen) | 0.4 |
| NN062441 | DSM 17236 | *Bacillus licheniformis* | GalliPro Tect (Chr. Hansen) | 0.9 |
| NN062439 | | *Bacillus amyloliquefaciens* | Clostat (Kemin) | 2.1 |

What is claimed is:

1. A plurality of granules comprising calcium carbonate and spores of *Bacillus subtilis* DSM 29870.

2. The granules of claim 1, further comprising sucrose.

3. The granules of claim 1, further comprising sodium aluminum silicate.

4. A plurality of granules consisting essentially of (a) calcium carbonate, (b) spores of *Bacillus subtilis* DSM 29870, (c) sucrose, and, optionally, (d) sodium aluminum silicate.

5. The granules of claim 1, comprising about $1\times10^4$ to about $1\times10^{18}$ colony-forming units (CFU) of said *Bacillus subtilis* DSM 29870 per gram of said granules.

6. An animal feed comprising the granules of claim 1.

7. A pelleted animal feed comprising the granules of claim 1.

8. A mash animal feed comprising the granules of claim 1.

9. The animal feed of claim 6, comprising about $1\times10^4$ to about $1\times10^{14}$ colony-forming units (CFU) of said *Bacillus subtilis* DSM 29870 per kilogram of said animal feed.

10. The animal feed of claim 6, comprising about $1\times10^6$ to about $1\times10^{12}$ colony-forming units (CFU) of said *Bacillus subtilis* DSM 29870 per kilogram of said animal feed.

11. The animal feed of claim 6, wherein said animal feed comprises a forage.

12. A method comprising administering the granules of claim 1 to an animal.

13. The method of claim 12, wherein said animal is monogastric.

14. The method of claim 12, wherein said animal is a poultry animal.

15. The method of claim 12, wherein said animal is a pig.

16. A method comprising mixing the granules of claim 1 with one or more animal feed ingredient to produce an animal feed composition.

17. The method of claim 16, wherein said animal feed composition comprises about $1\times10^4$ to about $1\times10^{14}$ colony-forming units (CFU) of said *Bacillus subtilis* DSM 29870 per kilogram of said animal feed composition.

18. The method of claim 16, wherein said animal feed composition comprises about $1\times10^6$ to about $1\times10^{12}$ colony-forming units (CFU) of said *Bacillus subtilis* DSM 29870 per kilogram of said animal feed composition.

* * * * *

SEQUENCE LISTING

```
Sequence total quantity: 36
SEQ ID NO: 1            moltype = DNA  length = 1698
FEATURE                 Location/Qualifiers
source                  1..1698
                        mol_type = genomic DNA
                        organism = Bacillus subtilis
CDS                     1..1698
                        protein_id = 36
                        translation = SIDEALAGYCTDINIQIEKDNSITVVDNGRGIPVGIHEKMGRPAVE
                         VIMTVLHAGGKFDGSGYKVSGGLHGVGASVVNALSTELVVTVHRDGKIHRQTYKRGVPV
                         SDLEIIGETDHSGTTTHFVPDPEIFTETTVYDYDLLANRVRELAFLTKGVNITIEDKRE
                         GQERKNEYHYEGGIKSYVEYLNRSKEVVHEEPIYIEGEKDGITVEVALQYNDSYTSNIY
                         SFTNNINTYEGGTHEAGFKTGLTRVINDYARKKGLIKENDPNLSGDDVREGLTAIISIK
                         HPDPQFEGQTKTKLGNSEARTITDTLFSAALETFMLENPDAAKKIVDKGLMAARARMAA
                         KKARELTRRKSALEISNLPGKLADCSSKDPSISELYIVEGDSAGGSAKQGRDRHFQAIL
                         PLRGKILNVEKARLDKILSNNEVRSMITALGTGIGEDFNLGKARYHKVVIMTDADVDGA
                         HIRTLLLTFFYRYMRQIIENGYVYIAQPPLYKVQQGKRVEYAYNDKELDDLLKTLPQTP
                         KPGLQRYKGLGEMNATQLWETTMDPSSRTLLQVTLEDAMDADETFEML
SEQUENCE: 1
agtattgacg aagccctcgc cggttattgt acggatatca atatccaaat cgaaaaagac  60
```

```
aacagcatca cggtggtaga taacggccgc ggtattccag ttggtattca tgaaaaaatg  120
ggccggcctg cggtagaggt cattatgacg gtgcttcatg ccggagggaa atttgacgga  180
agcggctata aagtatccgg aggattgcac ggtgtaggtg cgtcagtcgt aaacgcgctt  240
tcaaccgagc ttgttgtgac ggtacaccgt gacggaaaaa tccaccgtca aacctataaa  300
cgcggagttc cggtttcaga ccttgaaatc attggcgaaa cagatcattc aggaacgacg  360
acacattttg tcccagatcc tgagattttc acagaaacaa ctgtgtatga ttatgatctg  420
cttgctaacc gtgtgcgcga attagccttt ttgacaaaag gcgtaaacat cacgattgaa  480
gataaacgtg aaggacaaga gcgcaaaaat gagtaccatt acgaaggcgg aattaaaagt  540
tatgtagagt atttaaaccg ttctaaagaa gttgtccatg aagagccgat ttacattgaa  600
ggcgaaaagg acggcattac ggttgaagtg gctttgcaat ataatgacag ctacacaagc  660
aacatttact cgtttacaaa taacattaac acgtatgaag gcgggaccca cgaagcaggc  720
ttcaaaacgg gcctgactcg tgtgatcaat gattacgcca gaaaaaaagg gctcattaaa  780
gaaaatgatc cgaacttaag cggtgacgac gtaagagaag ggctgaccgc gattatttcc  840
atcaaacacc ctgatccgca gtttgaaggc caaacgaaaa caaaactagg caactcggaa  900
gcgcggacga tcaccgatac gttattttct gcggcattgg aaacatttat gctggaaaat  960
ccagatgcgg ccaaaaaaat tgtcgacaaa ggtttgatgg cggcaagagc aagaatggct  1020
gcgaaaaaag cgcgtgaatt aacacgccgc aagagtgctt tggaaatttc aaaccttccc  1080
ggtaagctag cggactgctc atcaaaagat ccgagcattt ccgagttata tatcgtagag  1140
ggtgactctg ccggaggatc agctaaacaa ggccgcgaca gacatttcca agccattttg  1200
ccgcttagag gtaaaatctt aaacgttgaa aaagcgagat tggacaaaat cctttccaac  1260
aacgaagttc gttctatgat cacagcactc ggaacaggta taggggaaga tttcaacttg  1320
gggaaagccc gttaccataa agttgtcatt atgactgatg ccgacgttga cggcgcgcac  1380
atcagaacac tgctgttaac gttcttttac agatatatgc gccaaattat tgaaaatggc  1440
tacgtgtata ttgcgcagcc gccgctctac aaggttcaac agggaaaacg tgttgaatat  1500
gcatataatg acaaagaact tgatgatctg ttgaaaactc ttcctcaaac gcctaagcct  1560
ggcttgcagc gttataaagg tcttggagaa atgaatgcga cccagctatg ggagacaacc  1620
atggatccga gctccagaac acttcttcag gtaactcttg aagatgcaat ggatgccgat  1680
gagacatttg aaatgctg                                              1698

SEQ ID NO: 2           moltype = AA  length = 566
FEATURE                Location/Qualifiers
source                 1..566
                       mol_type = protein
                       organism = Bacillus subtilis
SEQUENCE: 2
SIDEALAGYC TDINIQIEKD NSITVVDNGR GIPVGIHEKM GRPAVEVIMT VLHAGGKFDG  60
SGYKVSGGLH GVGASVVNAL STELVVTVHR DGKIHRQTYK RGVPVSDLEI IGETDHSGTT  120
THFVPDPEIF TETTVYDYDL LANRVRELAF LTKGVNITIE DKREGQERKN EYHYEGGIKS  180
YVEYLNRSKE VVHEEPIYIE GEKDGITVEV ALQYNDSYTS NIYSFTNNIN TYEGGTHEAG  240
FKTGLTRVIN DYARKKGLIK ENDPNLSGDD VREGLTAIIS IKHPDPQFEG QTKTKLGNSE  300
ARTITDTLFS AALETFMLEN PDAAKKIVDK GLMAARARMA AKKARELTRR KSALEISNLP  360
GKLADCSSKD PSISELYIVE GDSAGGSAKQ GRDRHFQAIL PLRGKILNVE KARLDKILSN  420
NEVRSMITAL GTGIGEDFNL GKARYHKVVI MTDADVDGAH IRTLLLTFFY RYMRQIIENG  480
YVYIAQPPLY KVQQGKRVEY AYNDKELDDL LKTLPQTPKP GLQRYKGLGE MNATQLWETT  540
MDPSSRTLLQ VTLEDAMDAD ETFEML                                     566

SEQ ID NO: 3           moltype = DNA  length = 3582
FEATURE                Location/Qualifiers
source                 1..3582
                       mol_type = genomic DNA
                       organism = Bacillus subtilis
CDS                    1..3582
SEQUENCE: 3
ttgacaggtc aactagttca gtatggacga caccgccagc gcagaagcta tgctcgcatt  60
agcgaagtgt tagaattacc aaatctcatt gaaattcaaa cctcttctta tcagtggttt  120
cttgatgagg gtcttagaga gatgtttcaa gacatatcac caattgagga tttcactggt  180
aacctctctc ttgagttcat tgattatagt ttaggtgagc ctaaatatcc tgtagaggaa  240
tcaaaagaac gtgatgtgac ttactcagct ccgctaagag tgaaggttcg tttaattaac  300
aaagaaactg gagaggtaaa agaccaagat gtcttcatgg gggatttccc gattatgaca  360
gatacaggta cttttatcat taatggtgcg gaacgtgtaa tcgtttccca gcttgttcgg  420
tctccaagtg tatatttcag tggtaaagta gacaaaaacg gtaaaaaagg ttttaccgca  480
actgtcattc caaaccgtgg cgcatggtta gaatacgaaa ctgatgcgaa agatgttgtt  540
tatgtccgca ttgatcgcac acgtaagttg ccggttacgg ttcttttgcg tgctctcggc  600
ttcggttccg atcaagagat tcttgatctc gtaggagaaa atgaatacct gcgaaatacg  660
cttgataaag ataacacaga aaatagcgac aaagctttgc ttgaaattta cgaacgtctc  720
cgtcctggag agccacctac agttgaaaat gcgaaaagct tgcttgattc gcgtttcttt  780
gatccgaaac gttacgatct tgccaatgta ggacgctata aaattaataa aaaacttcat  840
attaagaatc gcctctttaa tcagagactt gctgaaacgc ttgttgaccc tgaaacagga  900
gaaatccttg ctgaaaaagg tcagattctt gatagaagaa cacttgataa agtactgcca  960
tacttagaaa gcggaatcgg tttcagaaag ctgtatccaa atggcggtgt tgttgaagat  1020
gaagtaactc ttcaatcgat taaaatctat gctccgactg accaagaagg agaacaggtt  1080
atcaatgtaa tcggcaatgc ttacattgaa gaagagatta aaaacattac gcctgctgat  1140
attatttcct ctatcagcta cttcttcaac ctgctgcacg gagtaggcga tacagatgat  1200
atcgatcatc ttggaaaccg ccgtttacgt tctgtaggtg aacttctcca gaaccaattc  1260
cgtatcgggt taagccgtat ggagcgtgtg gttcgtgaga gaatgtcaat tcaagatacg  1320
aatacaatta cgcctcagca gttgatcaat attcgtcctg ttattgcgtc cattaaagag  1380
ttctttggaa gctctcagct ttcccagttc atggaccaga cgaacccgct tgctgaatta  1440
acgcataagc gtcgtctgtc agcattagga ccaggcggat tgacacgtga acgtgccgga  1500
atggaagtgc gtgacgttca ctactcccac tatggccgta tgtgtccgat tgaaacacct  1560
```

```
gagggtccaa acatcggttt gatcaactcg ctttcatctt atgcaaaagt aaaccgtttt  1620
ggtttcatcg aaacgcctta tcgccgtgtt gaccctgaaa cagggaaggt aacgggcaga  1680
atcgattact taactgctga tgaagaggat aactatgttg tcgctcaggc gaacgctcgt  1740
cttgatgacg atggctcatt tattgatgac agcattatcg cccgtttccg cggggagaac  1800
accgttgttt ccagaaaccg tgtggattac atggatgtat cacctaagca ggttgtttct  1860
gctgcgacag catgtatccc gttcctagaa aacgatgact ccaaccgtgc cctcatggga  1920
gcaaacatgc aacgtcaggc tgtgcctttg atgcagccgg aagcgccgtt cgttggaact  1980
ggtatggaat atgtatcagg taaagactct ggtgccgctg ttatttgtaa acaccctggt  2040
atcgttgaac gcgtagaagc gaagaacgtt tgggttcgcc gttatgaaga agtagatggt  2100
caaaaagtaa aagggaacct ggataaatac agcatgctga aatttgtccg ctccaaccaa  2160
ggtacttgct acaatcaacg tccgatcgta agtgtcggcg atgaagtggt aaaaggagaa  2220
atccttgctg acggtccttc tatggagctt ggtgaacttg cacttggccg taacgtaatg  2280
gttggcttca tgacttggga tggctacaac tatgaggatg ccatcatcat gagtgaacgc  2340
cttgtgaagg atgatgttta tacatctatc cacattgaag aatatgaatc agaagcacgc  2400
gatacgaaac ttggacctga agaaatcact cgcgatattc caaacgtcgg tgaagatgcg  2460
cttcgcaatc ttgatgaccg cggaatcatc cgtattgggg cagaagtgaa agacggagat  2520
cttcttgttg gtaaagtaac gcctaaaggt gtaactgaac tgactgctga agaacgcctg  2580
cttcacgcca tctttggtga aaaggcccgc gaggttcgtg atacttctct tcgtgtgcct  2640
cacggcggcg gcggaattat ccacgacgtt aaagtcttca atcgtgaaga cggagatgaa  2700
cttcctccag gcgttaacca gttggtacgt gtgtatatcg ttcagaaacg taagatttct  2760
gaaggggata aaatggccgg tcgtcacggt aacaaaggtg ttatctctaa gattcttcct  2820
gaagaggata tgccttacct tcctgacggc acaccaattg atatcatgct taacccgctg  2880
ggcgtaccat cacgtatgaa catcgggcag gtattggagc tccatatggg tatggccgct  2940
cgttatctcg gcatccacat tgcgtcaccg gtatttgacg gagcgcgtga agaggatgtt  3000
tgggaaacac ttgaagaagc cggaatgtct cgtgacgcca aaacggttct ttacgacggg  3060
cgtagcggag agccgtttga taaccgtgta tctgttggta ttatgtacat gattaaactg  3120
gctcacatgg ttgacgataa acttcatgcg cgctctacag gcccttactc acttgttacg  3180
cagcagcctc ttggcggtaa agcgcaattt ggcggacagc gttttggtga gatggaggtt  3240
tgggcacttg aagcttacgg tgcggcttac actcttcaag aaattctgac tgttaaatct  3300
gatgacgtgg ttggacgtgt gaaaacatac gaagccatcg ttaaaggcga caacgttcct  3360
gaaccaggtg ttccggaatc attcaaagta ttaatcaagg aacttcaaag cttaggtatg  3420
gatgtcaaaa tcctttctgg tgatgaagaa gaaatagaaa tgagagattt agaagacgaa  3480
gaagatgcaa aacaagctga cggcctggcg ttatcaggtg atgaagagcc ggaggaaaca  3540
gcatctgcag acgttgaacg agatgtagta acaaaagaat aa                      3582

SEQ ID NO: 4           moltype = AA  length = 1193
FEATURE                Location/Qualifiers
source                 1..1193
                       mol_type = protein
                       organism = Bacillus subtilis
SEQUENCE: 4
LTGQLVQYGR HRQRRSYARI SEVLELPNLI EIQTSSYQWF LDEGLREMFQ DISPIEDFTG  60
NLSLEFIDYS LGEPKYPVEE SKERDVTYSA PLRVKVRLIN KETGEVKDQD VFMGDFPIMT  120
DTGTFIINGA ERVIVSQLVR SPSVYFSGKV DKNGKKGFTA TVIPNRGAWL EYETDAKDVV  180
YVRIDRTRKL PVTVLLRALG FGSDQEILDL VGENEYLRNT LDKDNTENSD KALLEIYERL  240
RPGEPPTVEN AKSLLDSRFF DPKRYDLANV GRYKINKKLH IKNRLFNQRL AETLVDPETG  300
EILAEKGQIL DRRTLDKVLP YLESGIGFRK LYPNGGVVED EVTLQSIKIY APTDQEGEQV  360
INVIGNAYIE EEIKNITPAD IISSISYFFN LLHGVGDTDD IDHLGNRRLR SVGELLQNQF  420
RIGLSRMERV VRERMSIQDT NTITPQQLIN IRPVIASIKE FFGSSQLSQF MDQTNPLAEL  480
THKRRLSALG PGGLTRERAG MEVRDVHYSH YGRMCPIETP EGPNIGLINS LSSYAKVNRF  540
GFIETPYRRV DPETGKVTGR IDYLTADEED NYVVAQANAR LDDDGSFIDD SIIARFRGEN  600
TVVSRNRVDY MDVSPKQVVS AATACIPFLE NDDSNRALMG ANMQRQAVPL MQPEAPFVGT  660
GMEYVSGKDS GAAVICKHPG IVERVEAKNV WVRRYEEVDG QKVKGNLDKY SMLKFVRSNQ  720
GTCYNQRPIV SVGDEVVKGE ILADGPSMEL GELALGRNVM VGFMTWDGYN YEDAIIMSER  780
LVKDDVYTSI HIEEYESEAR DTKLGPEEIT RDIPNVGEDA LRNLDDRGII RIGAEVKDGD  840
LLVGKVTPKG VTELTAEERL LHAIFGEKAR EVRDTSLRVP HGGGGIIHDV KVFNREDGDE  900
LPPGVNQLVR VYIVQKRKIS EGDKMAGRHG NKGVISKILP EEDMPYLPDG TPIDIMLNPL  960
GVPSRMNIGQ VLELHMGMAA RYLGIHIASP VFDGAREEDV WETLEEAGMS RDAKTVLYDG  1020
RSGEPFDNRV SVGIMYMIKL AHMVDDKLHA RSTGPYSLVT QQPLGGKAQF GGQRFGEMEV  1080
WALEAYGAAY TLQEILTVKS DDVVGRVKTY EAIVKGDNVP EPGVPESFKV LIKELQSLGM  1140
DVKILSGDEE EIEMRDLEDE EDAKQADGLA LSGDEEPEET ASADVERDVV TKE          1193

SEQ ID NO: 5           moltype = DNA  length = 1548
FEATURE                Location/Qualifiers
source                 1..1548
                       mol_type = genomic DNA
                       organism = Bacillus subtilis
CDS                    1..1548
SEQUENCE: 5
tatgcaatga gcgttattgt gtcccgtgct cttccagatg tacgtgacgg tttaaaaccg  60
gttcacagac ggattttgta tgcaatgaat gatttgggca tgacgagtga caagccatat  120
aaaaaatccg cgcgtatcgt cggagaagtt atcgggaaat accacccgca cggtgattca  180
gcggtatatg aatccatggt cagaatggcg caggatttta actaccgtta catgctcgtt  240
gacggtcacg ggaacttcgg ttctgttgac ggagactcag cggctgccat gcgttataca  300
gaagcaagaa tgtctaagat ctcgatggaa attcttcgag atatcacaaa agacacaatc  360
gattatcagg acaactatga tgggtcagaa agagaacccg tcgttatgcc ttcaaggttc  420
ccgaatctgc tcgtgaacgg tgctgccggt attgcggtag gtatggcaac aaacatccct  480
ccgcaccagc ttggggaaat cattgacggt gtacttgctg tcagtgagaa cccggacatt  540
acaatccctg agctgatgga agtcattcca gggcctgatt tcccgactgc gggtcaaatc  600
```

-continued

```
ttgggacgca gcggtatccg gaaagcatac gaatctggcc gaggctctat tacgattcgg  660
gcaaaagctg agatcgaaca aacatcttca ggtaaagaaa gaattatcgt tacagagtta  720
ccttaccaag taaataaggc gaaattaatc gagaaaattg ctgatctcgt tagggacaaa  780
aagatagagg gcatcacaga tctgcgtgat gagtcagatc gtacaggtat gagaattgtc  840
attgaaatca gacgcgatgc caatgcaaat gttattctaa ataacctata caaacaaact  900
gcgctacaaa catcttttgg tatcaacctg cttgcgcttg ttgacggtca gccgaaagtt  960
ttaaatctaa agcaatgcct agagcattac cttgaccatc aaaaagtcgt catcagacgc  1020
cgtacagcat atgaattgcg taaagcggaa gcgagagctc atatcttgga aggtttgaga  1080
attgctctcg atcatctcga tgcagttatt tctcttatcc gtaattctca aacggctgaa  1140
atagcgagaa caggtctaat tgaacaattc tcactgacag agaagcaagc acaagcgatc  1200
ctcgatatga ggctgcagcg tttaacagga ctagaacgtg aaaagatcga agaagaatac  1260
caatctcttg ttaaattaat tgcagagcta aaagacattt tggcaaatga atataaagtg  1320
cttgagatca tccgtgaaga actcactgaa atcaaagagc gtttcaacga tgaaagacgc  1380
acggagatcg tcacttctgg actagaaaca attgaagatg aagatcttat tgagagagaa  1440
aatatcgtcg tcactctgac acacaacggg tacatcaaac gtcttcctgc atcaacttac  1500
cgcagtcaaa aacgaggcgg aaaaggtgta cagggaatgg gaacaaac              1548
```

```
SEQ ID NO: 6            moltype = AA  length = 516
FEATURE                 Location/Qualifiers
source                  1..516
                        mol_type = protein
                        organism = Bacillus subtilis
SEQUENCE: 6
YAMSVIVSRA LPDVRDGLKP VHRRILYAMN DLGMTSDKPY KKSARIVGEV IGKYHPHGDS  60
AVYESMVRMA QDFNYRYMLV DGHGNFGSVD GDSAAAMRYT EARMSKISME ILRDITKDTI  120
DYQDNYDGSE REPVVMPSRF PNLLVNGAAG IAVGMATNIP PHQLGEIIDG VLAVSENPDI  180
TIPELMEVIP GPDFPTAGQI LGRSGIRKAY ESGRGSITIR AKAEIEQTSS GKERIIVTEL  240
PYQVNKAKLI EKIADLVRDK KIEGITDLRD ESDRTGMRIV IEIRRDANAN VILNNLYKQT  300
ALQTSFGINL LALVDGQPKV LNLKQCLEHY LDHQKVVIRR RTAYELRKAE ARAHILEGLR  360
IALDHLDAVI SLIRNSQTAE IARTGLIEQF SLTEKQAQAI LDMRLQRLTG LEREKIEEEY  420
QSLVKLIAEL KDILANEYKV LEIIREELTE IKERFNDERR TEIVTSGLET IEDEDLIERE  480
NIVVTLTHNG YIKRLPASTY RSQKRGGKGV QGMGTN                           516
```

```
SEQ ID NO: 7            moltype = DNA  length = 1527
FEATURE                 Location/Qualifiers
source                  1..1527
                        mol_type = genomic DNA
                        organism = Bacillus subtilis
CDS                     1..1527
SEQUENCE: 7
tatgcaatga gcgttatcgt gtcccgtgct cttccagatg tccgtgacgg tttaaaaccg  60
gttcacagac ggattttgta tgcaatgaac gatctgggca tgacaagtga caaggcttat  120
aaaaaatccg cgcgtatcgt cggagaagtt atcgggaaat accacccgca tggtgattca  180
gcggtatatg aatccatggt cagaatggcg caggatttca actatcgtta tatgctcgtt  240
gacggtcacg gaaacttcgg ttctgttgac ggggactcag cggctgccat gcgttatacg  300
gaagcaagaa tgtctaaaat ctcgatggaa attcttcgag acatcacaaa agacacaatc  360
gattatcagg acaactatga cggatcagaa agagaacctg tcgttatgcc ttcaagattc  420
ccgaatctgc ttgtaaacgg cgctgccgga attgcggtag gtatggcaac aaacattcct  480
ccgcaccagt tgggagaaat cattgacggt gtgcttgctg tcagtgaaaa tcctgaaatc  540
gcagtacagg agctcatgga gattattcct ggtcctgact tcccgactgc ggggcaaatt  600
ttgggccgaa gcggtattcg taaagcatac gaatcaggac gaggctcgat tacgatccgg  660
gcaaaagcgg agatcgaaca aacatcgtca ggaaaagaaa gaattgtcgt aacagaactt  720
ccataccaag taaataaagc aaaactaatc gaaaaaatcg ctgatcttgt cagagataag  780
aagatagaag gtattaccga tctgcgtgat gaatctgacc gcacaggtat gagaatcgtc  840
attgaaatca gaagagatgc caacgcgcat gtcattctaa ataatctata taagcaaaca  900
gctttgcaaa cttcttttgg tatcaatctg cttgcgcttg ttgacggaca gccaaaagtt  960
ttaaatttaa agcaatgctt ggagtattac ctagatcacc aaaaagtcgt aatcagacgc  1020
cgtactgctt atgaattgcg taaagcggag gcgagagcac atatcttgga aggattgaga  1080
attgctcttg atcatcttga tgcagttatt tcccttatcc gtaattctca aacggctgaa  1140
attgcgagaa caggattaat tgaacaattc tcgctgactg aaaaacaagc ccaagctatt  1200
cttgatatga gactgcagcg tttaacagga ttggaacgtg aaaagattga agaggagtac  1260
cgatcccttg ttaaattaat tgcagagctt aaagaaatct tggccaatga agaaaaagtg  1320
cttgagatca ttcgtgaaga actcatagaa attaaagagc gttttaacga tgaaagacgc  1380
actgagatcg tcactgccgg tcttgaaaca attgaagatg aagatctcat cgaaagagaa  1440
aacatcgttg tcaccctgac acacaacgga tatatcaaac gtctgcctgc ctcaacctac  1500
cgcagtcaaa agcgtggcgg aaaaggc                                     1527
```

```
SEQ ID NO: 8            moltype = AA  length = 509
FEATURE                 Location/Qualifiers
source                  1..509
                        mol_type = protein
                        organism = Bacillus subtilis
SEQUENCE: 8
YAMSVIVSRA LPDVRDGLKP VHRRILYAMN DLGMTSDKAY KKSARIVGEV IGKYHPHGDS  60
AVYESMVRMA QDFNYRYMLV DGHGNFGSVD GDSAAAMRYT EARMSKISME ILRDITKDTI  120
DYQDNYDGSE REPVVMPSRF PNLLVNGAAG IAVGMATNIP PHQLGEIIDG VLAVSENPEI  180
AVQELMEIIP GPDFPTAGQI LGRSGIRKAY ESGRGSITIR AKAEIEQTSS GKERIVVTEL  240
PYQVNKAKLI EKIADLVRDK KIEGITDLRD ESDRTGMRIV IEIRRDANAH VILNNLYKQT  300
ALQTSFGINL LALVDGQPKV LNLKQCLEYY LDHQKVVIRR RTAYELRKAE ARAHILEGLR  360
```

```
IALDHLDAVI SLIRNSQTAE IARTGLIEQF SLTEKQAQAI LDMRLQRLTG LEREKIEEEY  420
RSLVKLIAEL KEILANEEKV LEIIREELIE IKERFNDERR TEIVTAGLET IEDEDLIERE  480
NIVVTLTHNG YIKRLPASTY RSQKRGGKG                                   509

SEQ ID NO: 9            moltype = DNA  length = 1507
FEATURE                 Location/Qualifiers
source                  1..1507
                        mol_type = genomic DNA
                        organism = Bacillus subtilis
SEQUENCE: 9
gacgaacgct ggcggcgtgc ctaatacatg caagtcgagc ggacagatgg gagcttgctc  60
cctgatgtta gcggcggacg ggtgagtaac acgtgggtaa cctgcctgta agactgggat  120
aactccggga aaccggggct aataccggat gcttgtttga accgcatggt tcaaacataa  180
aaggtggctt cggctaccac ttacagatgg acccgcggcg cattagctag ttggtgaggt  240
aacggctcac caaggcaacg atgcgtagcc gacctgagag ggtgatcggc cacactggga  300
ctgagacacg gcccagactc ctacgggagg cagcagtagg gaatcttccg caatggacga  360
aagtctgacg gagcaacgcc gcgtgagtga tgaaggtttt cggatcgtaa agctctgttg  420
ttagggaaga acaagtaccg ttcgaatagg gcggtacctt gacggtacct aaccagaaag  480
ccacggctaa ctacgtgcca gcagccgcgg taatacgtag gtggcaagcg ttgtccggaa  540
ttattgggcg taaagggctc gcaggcggtt tcttaagtct gatgtgaaag cccccggctc  600
aaccggggag ggtcattgga aactggggaa cttgagtgca gaagaggaga gtggaattcc  660
acgtgtagcg gtgaaatgcg tagagatgtg gaggaacacc agtggcgaag gcgactctct  720
ggtctgtaac tgacgctgag gagcgaaagc gtggggagcg aacaggatta gataccctgg  780
tagtccacgc cgtaaacgat gagtgctaag tgttaggggg tttccgcccc ttagtgctgc  840
agctaacgca ttaagcactc cgcctgggga gtacggtcgc aagactgaaa ctcaaaggaa  900
ttgacggggg cccgcacaag cggtggagca tgtggtttaa ttcgaagcaa cgcgaagaac  960
cttaccaggt cttgacatcc tctgacaatc ctagagatag gacgtcccct tcgggggcag  1020
agtgacaggt ggtgcatggt tgtcgtcagc tcgtgtcgtg agatgttggg ttaagtcccg  1080
caacgagcgc aacccttgat cttagttgcc agcattcagt tgggcactct aaggtgactg  1140
ccggtgacaa accggaggaa ggtggggatg acgtcaaatc atcatgcccc ttatgacctg  1200
ggctacacac gtgctacaat ggacagaaca aagggcagcg aaaccgcgag gttaagccaa  1260
tcccacaaat ctgttctcag ttcggatcgc agtctgcaac tcgactgcgt gaagctggaa  1320
tcgctagtaa tcgcggatca gcatgccgcg gtgaatacgt tcccgggcct tgtacacacc  1380
gcccgtcaca ccacgagagt ttgtaacacc cgaagtcggt gaggtaacct tttaggagcc  1440
agccgccgaa ggtgggacag atgattgggg tgaagtcgta acaaggtagc cgtatcggaa  1500
ggtgcgg                                                           1507

SEQ ID NO: 10           moltype = DNA  length = 19
FEATURE                 Location/Qualifiers
source                  1..19
                        mol_type = other DNA
                        organism = synthetic construct
SEQUENCE: 10
gagtttgatc ctggctcag                                              19

SEQ ID NO: 11           moltype = DNA  length = 20
FEATURE                 Location/Qualifiers
source                  1..20
                        mol_type = other DNA
                        organism = synthetic construct
SEQUENCE: 11
agaaaggagg tgatccagcc                                             20

SEQ ID NO: 12           moltype = DNA  length = 21
FEATURE                 Location/Qualifiers
source                  1..21
                        mol_type = other DNA
                        organism = synthetic construct
SEQUENCE: 12
atctaatcct gtttgctccc c                                           21

SEQ ID NO: 13           moltype = DNA  length = 15
FEATURE                 Location/Qualifiers
source                  1..15
                        mol_type = other DNA
                        organism = synthetic construct
SEQUENCE: 13
tacgggaggc agcag                                                  15

SEQ ID NO: 14           moltype = DNA  length = 17
FEATURE                 Location/Qualifiers
source                  1..17
                        mol_type = other DNA
                        organism = synthetic construct
variation               9
                        note = n=a or g
SEQUENCE: 14
cggtgtgtnc aaggccc                                                17
```

-continued

```
SEQ ID NO: 15            moltype = DNA  length = 16
FEATURE                  Location/Qualifiers
source                   1..16
                         mol_type = other DNA
                         organism = synthetic construct
SEQUENCE: 15
caacgagcgc aaccct                                                    16

SEQ ID NO: 16            moltype = DNA  length = 20
FEATURE                  Location/Qualifiers
source                   1..20
                         mol_type = other DNA
                         organism = synthetic construct
variation                3
                         note = n=a or c
variation                15
                         note = n=g or c
SEQUENCE: 16
gtntgggaaa ttgtngacaa                                                20

SEQ ID NO: 17            moltype = DNA  length = 20
FEATURE                  Location/Qualifiers
source                   1..20
                         mol_type = other DNA
                         organism = synthetic construct
variation                8
                         note = n=c or t
variation                14
                         note = n= a or g
variation                17
                         note = n=a or g
SEQUENCE: 17
gcggttcnac tttntcnccc                                                20

SEQ ID NO: 18            moltype = DNA  length = 20
FEATURE                  Location/Qualifiers
modified_base            9
                         mod_base = i
source                   1..20
                         mol_type = other DNA
                         organism = synthetic construct
variation                3
                         note = n=c or t
variation                6
                         note = n=c or t
variation                18
                         note = n=c or t
SEQUENCE: 18
ggnatnccng tcggcatnca                                                20

SEQ ID NO: 19            moltype = DNA  length = 20
FEATURE                  Location/Qualifiers
source                   1..20
                         mol_type = other DNA
                         organism = synthetic construct
variation                6
                         note = n=g or c
variation                9
                         note = n=c or t
variation                12
                         note = n=c or t
variation                18
                         note = n=a or c
SEQUENCE: 19
tccatngtng tntcccanag                                                20

SEQ ID NO: 20            moltype = DNA  length = 20
FEATURE                  Location/Qualifiers
source                   1..20
                         mol_type = other DNA
                         organism = synthetic construct
SEQUENCE: 20
tacgcatgat ttgaggggtg                                                20

SEQ ID NO: 21            moltype = DNA  length = 21
FEATURE                  Location/Qualifiers
source                   1..21
                         mol_type = other DNA
                         organism = synthetic construct
```

-continued

```
SEQUENCE: 21
aaccgatgtc acttgccttt a                                              21

SEQ ID NO: 22          moltype = DNA  length = 20
FEATURE                Location/Qualifiers
source                 1..20
                       mol_type = other DNA
                       organism = synthetic construct
SEQUENCE: 22
ttaattaaca aagaaactgg                                                20

SEQ ID NO: 23          moltype = DNA  length = 20
FEATURE                Location/Qualifiers
source                 1..20
                       mol_type = other DNA
                       organism = synthetic construct
SEQUENCE: 23
atgtaatcgg caatgcttac                                                20

SEQ ID NO: 24          moltype = DNA  length = 20
FEATURE                Location/Qualifiers
source                 1..20
                       mol_type = other DNA
                       organism = synthetic construct
SEQUENCE: 24
aggctgtgcc tttgatgcag                                                20

SEQ ID NO: 25          moltype = DNA  length = 20
FEATURE                Location/Qualifiers
source                 1..20
                       mol_type = other DNA
                       organism = synthetic construct
SEQUENCE: 25
gaaacgtaag atttctgaag                                                20

SEQ ID NO: 26          moltype = DNA  length = 20
FEATURE                Location/Qualifiers
source                 1..20
                       mol_type = other DNA
                       organism = synthetic construct
SEQUENCE: 26
gagagcacgc aaaagaaccg                                                20

SEQ ID NO: 27          moltype = DNA  length = 20
FEATURE                Location/Qualifiers
source                 1..20
                       mol_type = other DNA
                       organism = synthetic construct
SEQUENCE: 27
gtttcaatcg gacacatacg                                                20

SEQ ID NO: 28          moltype = DNA  length = 20
FEATURE                Location/Qualifiers
source                 1..20
                       mol_type = other DNA
                       organism = synthetic construct
SEQUENCE: 28
ccgtcagcaa ggatttctcc                                                20

SEQ ID NO: 29          moltype = DNA  length = 20
FEATURE                Location/Qualifiers
source                 1..20
                       mol_type = other DNA
                       organism = synthetic construct
SEQUENCE: 29
tccataccta agctttgaag                                                20

SEQ ID NO: 30          moltype = DNA  length = 19
FEATURE                Location/Qualifiers
source                 1..19
                       mol_type = other DNA
                       organism = synthetic construct
variation              9
                       note = n=a, c, g or t
variation              12
                       note = n=a, c, g or t
variation              15
                       note = n= c or t
SEQUENCE: 30
```

```
gaaggcggna cncangaag                                                    19

SEQ ID NO: 31          moltype = DNA  length = 19
FEATURE                Location/Qualifiers
source                 1..19
                       mol_type = other DNA
                       organism = synthetic construct
variation              5
                       note = n=a or g
variation              8
                       note = n=a, c, g or t
variation              11
                       note = n=a, c, g or t
SEQUENCE: 31
cttcntgngt nccgccttc                                                    19

SEQ ID NO: 32          moltype = DNA  length = 1577
FEATURE                Location/Qualifiers
source                 1..1577
                       mol_type = other DNA
                       organism = Bacillus subtilis
CDS                    1..1575
SEQUENCE: 32
agtattgacg aagccctcgc cggttattgt acggatatca atatccaaat cgaaaaagac  60
aacagcatca cggtggtaga taacggccgc ggtattccag ttggtattca tgaaaaaatg  120
ggccggcctg cggtagaggt cattatgacg gtgcttcatg ccggagggaa atttgacgga  180
agcggctata aagtatccgg aggattgcac ggtgtaggtg cgtcagtcgt aaacgcgctt  240
tcaaccgagc ttgttgtgac ggtacaccgt gacggaaaaa tccaccgtca aacctataaa  300
cgcggagttc cggtttcaga ccttgaaatc attggcgaaa cagatcattc aggaacgacg  360
acacattttg tcccagatcc tgagattttc acagaaacaa ctgtgtatga ttatgatctg  420
cttgctaacc gtgtgcgcga attagccttt ttgacaaaag gcgtaaacat cacgattgaa  480
gataaacgtg aaggacaaga gcgcaaaaat gagtaccatt acgaaggcgg aattaaaagt  540
tatgtagagt atttaaaccg ttctaaagaa gttgtccatg aagagccgat ttacattgaa  600
ggcgaaaagg acggcattac ggttgaagtg gctttgcaat ataatgacag ctacacaagc  660
aacatttact cgtttacaaa taacattaac acgtatgaag gcgggaccca cgaagcaggc  720
ttcaaaacgg gcctgactcg tgtgatcaat gattacgcca gaaaaaaagg gctcattaaa  780
gaaaatgatc cgaacttaag cggtgacgac gtaagagaag ggctgaccgc gattatttcc  840
atcaaacacc ctgatccgca gtttgaaggc caaacgaaaa caaaactagg caactcggaa  900
gcgcggacga tcaccgatac gttattttct gcggcattgg aaacatttat gctggaaaat  960
ccagatgcgg ccaaaaaaat tgtcgacaaa ggtttgatgg cggcaagagc aagaatggct  1020
gcgaaaaaag cgcgtgaatt aacacgccgc aagagtgctt tggaaatttc aaaccttccc  1080
ggtaagctag cggactgctc atcaaaagat ccgagcattt ccgagttata tatcgtagag  1140
ggtgactctg ccggaggatc agctaaacaa ggccgcgaca gacatttcca agccattttg  1200
ccgcttagag gtaaaatctt aaacgttgaa aaagcgagat tggacaaaat cctttccaac  1260
aacgaagttc gttctatgat cacagcactc ggaacaggta taggggaaga tttcaacttg  1320
gggaaagccc gttaccataa agttgtcatt atgactgatg ccgacgttga cggcgcgcac  1380
atcagaacac tgctgttaac gttcttttac agatatatgc gccaaattat tgaaaatggc  1440
tacgtgtata ttgcgcagcc gccgctctac aaggttcaac agggaaaacg tgttgaatat  1500
gcatataatg acaaagaact tgatgatctg ttgaaaactc ttcctcaaac gcctaagcct  1560
ggcttgcagc gttataa                                                      1577

SEQ ID NO: 33          moltype = AA  length = 525
FEATURE                Location/Qualifiers
source                 1..525
                       mol_type = protein
                       organism = Bacillus subtilis
SEQUENCE: 33
SIDEALAGYC TDINIQIEKD NSITVVDNGR GIPVGIHEKM GRPAVEVIMT VLHAGGKFDG  60
SGYKVSGGLH GVGASVVNAL STELVVTVHR DGKIHRQTYK RGVPVSDLEI IGETDHSGTT  120
THFVPDPEIF TETTVYDYDL LANRVRELAF LTKGVNITIE DKREGQERKN EYHYEGGIKS  180
YVEYLNRSKE VVHEEPIYIE GEKDGITVEV ALQYNDSYTS NIYSFTNNIN TYEGGTHEAG  240
FKTGLTRVIN DYARKKGLIK ENDPNLSGDD VREGLTAIIS IKHPDPQFEG QTKTKLGNSE  300
ARTITDTLFS AALETFMLEN PDAAKKIVDK GLMAARARMA AKKARELTRR KSALEISNLP  360
GKLADCSSKD PSISELYIVE GDSAGGSAKQ GRDRHFQAIL PLRGKILNVE KARLDKILSN  420
NEVRSMITAL GTGIGEDFNL GKARYHKVVI MTDADVDGAH IRTLLLTFFY RYMRQIIENG  480
YVYIAQPPLY KVQQGKRVEY AYNDKELDDL LKTLPQTPKP GLQRY                      525

SEQ ID NO: 34          moltype = DNA  length = 3368
FEATURE                Location/Qualifiers
source                 1..3368
                       mol_type = other DNA
                       organism = Bacillus subtilis
CDS                    1..3366
SEQUENCE: 34
ttgacaggtc aactagttca gtatggacga caccgccagc gcagaagcta tgctcgcatt  60
agcgaagtgt tagaattacc aaatctcatt gaaattcaaa cctcttctta tcagtggttt  120
cttgatgagg gtcttagaga gatgtttcaa gacatatcac caattgagga tttcactggt  180
aacctctctc ttgagttcat tgattatagt ttaggtgagc ctaaatatcc tgtagaggaa  240
tcaaaagaac gtgatgtgac ttactcagct ccgctaagag tgaaggttcg tttaattaac  300
```

-continued

```
aaagaaactg gagaggtaaa agaccaagat gtcttcatgg gggatttccc gattatgaca  360
gatacaggta cttttatcat taatggtgcg gaacgtgtaa tcgtttccca gcttgttcgg  420
tctccaagtg tatatttcag tggtaaagta gacaaaaacg gtaaaaaagg ttttaccgca  480
actgtcattc caaaccgtgg cgcatggtta gaatacgaaa ctgatgcgaa agatgttgtt  540
tatgtccgca ttgatcgcac acgtaagttg ccggttacgg ttcttttgcg tgctctcggc  600
ttcggttccg atcaagagat tcttgatctc gtaggagaaa atgaatacct gcgaaatacg  660
cttgataaag ataacacaga aaatagcgac aaagctttgc ttgaaattta cgaacgtctc  720
cgtcctggag agccacctac agttgaaaat gcgaaaagct tgcttgattc gcgtttcttt  780
gatccgaaac gttacgatct tgccaatgta ggacgctata aattaataa aaaacttcat  840
attaagaatc gcctctttaa tcagagactt gctgaaacgc ttgttgaccc tgaaacagga  900
gaaatccttg ctgaaaaagg tcagattctt gatagaagaa cacttgataa agtactgcca  960
tacttagaaa gcggaatcgg tttcagaaag ctgtatccaa atggcggtgt tgttgaagat  1020
gaagtaactc ttcaatcgat taaaatctat gctccgactg accaagaagg agaacaggtt  1080
atcaatgtaa tcggcaatgc ttacattgaa gaagagatta aaaacattac gcctgctgat  1140
attatttcct ctatcagcta cttcttcaac ctgctgcacg gagtaggcga tacagatgat  1200
atcgatcatc ttggaaaccg ccgtttacgt tctgtaggtg aacttctcca gaaccaattc  1260
cgtatcgggt taagccgtat ggagcgtgtg gttcgtgaga gaatgtcaat tcaagatacg  1320
aatacaatta cgcctcagca gttgatcaat attcgtcctg ttattgcgtc cattaaagag  1380
ttctttggaa gctctcagct ttcccagttc atggaccaga cgaacccgct tgctgaatta  1440
acgcataagc gtcgtctgtc agcattagga ccaggcggat tgacacgtga acgtgccgga  1500
atggaagtgc gtgacgttca ctactcccac tatggccgta tgtgtccgat tgaaacacct  1560
gagggtccaa acatcggttt gatcaactcg ctttcatctt atgcaaaagt aaaccgtttt  1620
ggtttcatcg aaacgcctta tcgccgtgtt gaccctgaaa cagggaaggt aacgggcaga  1680
atcgattact taactgctga tgaagaggat aactatgttg tcgctcaggc gaacgctcgt  1740
cttgatgacg atggctcatt tattgatgac agcattatcg cccgtttccg cggggagaac  1800
accgttgttt ccagaaaccg tgtggattac atggatgtat cacctaagca ggttgtttct  1860
gctgcgacag catgtatccc gttcctagaa aacgatgact ccaaccgtgc cctcatggga  1920
gcaaacatgc aacgtcaggc tgtgcctttg atgcagccgg aagcgccgtt cgttggaact  1980
ggtatggaat atgtatcagg taaagactct ggtgccgctg ttatttgtaa acaccctggt  2040
atcgttgaac gcgtagaagc gaagaacgtt tgggttcgcc gttatgaaga agtagatggt  2100
caaaaagtaa aagggaacct ggataaatac agcatgctga aatttgtccg ctccaaccaa  2160
ggtacttgct acaatcaacg tccgatcgta agtgtcggcg atgaagtggt aaaaggagaa  2220
atccttgctg acggtccttc tatggagctt ggtgaacttg cacttggccg taacgtaatg  2280
gttggcttca tgacttggga tggctacaac tatgaggatg ccatcatcat gagtgaacgc  2340
cttgtgaagg atgatgttta tacatctatc cacattgaag aatatgaatc agaagcacgc  2400
gatacgaaac ttggacctga agaaatcact cgcgatattc caaacgtcgg tgaagatgcg  2460
cttcgcaatc ttgatgaccg cggaatcatc cgtattgggg cagaagtgaa agacggagat  2520
cttcttgttg gtaaagtaac gcctaaaggt gtaactgaac tgactgctga agaacgcctg  2580
cttcacgcca tctttggtga aaaggcccgc gaggttcgtg atacttctct tcgtgtgcct  2640
cacggcggcg gcggaattat ccacgacgtt aaagtcttca atcgtgaaga cggagatgaa  2700
cttcctccag gcgttaacca gttggtacgt gtgtatatcg ttcagaaacg taagatttct  2760
gaaggggata aaatggccgg tcgtcacggt aacaaaggtg ttatctctaa gattcttcct  2820
gaagaggata tgccttacct tcctgacggc acaccaattg atatcatgct taacccgctg  2880
ggcgtaccat cacgtatgaa catcgggcag gtattggagc tccatatggg tatggccgct  2940
cgttatctcg gcatccacat tgcgtcaccg gtatttgacg gagcgcgtga agaggatgtt  3000
tgggaaacac ttgaagaagc cggaatgtct cgtgacgcca aaacggttct ttacgacggg  3060
cgtagcggag agccgtttga taaccgtgta tctgttggta ttatgtacat gattaaactg  3120
gctcacatgg ttgacgataa acttcatgcg cgctctacag gcccttactc acttgttacg  3180
cagcagcctc ttggcggtaa agcgcaattt ggcggacagc gttttggtga gatggaggtt  3240
tgggcacttg aagcttacgg tgcggcttac actcttcaag aaattctgac tgttaaatct  3300
gatgacgtgg ttggacgtgt gaaaacatac gaagccatcg ttaaaggcga caacgttcct  3360
gaaccagg                                                          3368
```

```
SEQ ID NO: 35          moltype = AA  length = 1122
FEATURE                Location/Qualifiers
source                 1..1122
                       mol_type = protein
                       organism = Bacillus subtilis
SEQUENCE: 35
LTGQLVQYGR HRQRRSYARI SEVLELPNLI EIQTSSYQWF LDEGLREMFQ DISPIEDFTG  60
NLSLEFIDYS LGEPKYPVEE SKERDVTYSA PLRVKVRLIN KETGEVKDQD VFMGDFPIMT  120
DTGTFIINGA ERVIVSQLVR SPSVYFSGKV DKNGKKGFTA TVIPNRGAWL EYETDAKDVV  180
YVRIDRTRKL PVTVLLRALG FGSDQEILDL VGENEYLRNT LDKDNTENSD KALLEIYERL  240
RPGEPPTVEN AKSLLDSRFF DPKRYDLANV GRYKINKKLH IKNRLFNQRL AETLVDPETG  300
EILAEKGQIL DRRTLDKVLP YLESGIGFRK LYPNGGVVED EVTLQSIKIY APTDQEGEQV  360
INVIGNAYIE EEIKNITPAD IISSISYFFN LLHGVGDTDD IDHLGNRRLR SVGELLQNQF  420
RIGLSRMERV VRERMSIQDT NTITPQQLIN IRPVIASIKE FFGSSQLSQF MDQTNPLAEL  480
THKRRLSALG PGGLTRERAG MEVRDVHYSH YGRMCPIETP EGPNIGLINS LSSYAKVNRF  540
GFIETPYRRV DPETGKVTGR IDYLTADEED NYVVAQANAR LDDDGSFIDD SIIARFRGEN  600
TVVSRNRVDY MDVSPKQVVS AATACIPFLE NDDSNRALMG ANMQRQAVPL MQPEAPFVGT  660
GMEYVSGKDS GAAVICKHPG IVERVEAKNV WVRRYEEVDG QKVKGNLDKY SMLKFVRSNQ  720
GTCYNQRPIV SVGDEVVKGE ILADGPSMEL GELALGRNVM VGFMTWDGYN YEDAIIMSER  780
LVKDDVYTSI HIEEYESEAR DTKLGPEEIT RDIPNVGEDA LRNLDDRGII RIGAEVKDGD  840
LLVGKVTPKG VTELTAEERL LHAIFGEKAR EVRDTSLRVP HGGGGIIHDV KVFNREDGDE  900
LPPGVNQLVR VYIVQKRKIS EGDKMAGRHG NKGVISKILP EEDMPYLPDG TPIDIMLNPL  960
GVPSRMNIGQ VLELHMGMAA RYLGIHIASP VFDGAREEDV WETLEEAGMS RDAKTVLYDG  1020
RSGEPFDNRV SVGIMYMIKL AHMVDDKLHA RSTGPYSLVT QQPLGGKAQF GGQRFGEMEV  1080
WALEAYGAAY TLQEILTVKS DDVVGRVKTY EAIVKGDNVP EP                    1122
```

-continued

```
SEQ ID NO: 36          moltype = AA  length = 566
FEATURE                Location/Qualifiers
source                 1..566
                       mol_type = protein
                       organism = Bacillus subtilis
SEQUENCE: 36
SIDEALAGYC TDINIQIEKD NSITVVDNGR GIPVGIHEKM GRPAVEVIMT VLHAGGKFDG  60
SGYKVSGGLH GVGASVVNAL STELVVTVHR DGKIHRQTYK RGVPVSDLEI IGETDHSGTT  120
THFVPDPEIF TETTVYDYDL LANRVRELAF LTKGVNITIE DKREGQERKN EYHYEGGIKS  180
YVEYLNRSKE VVHEEPIYIE GEKDGITVEV ALQYNDSYTS NIYSFTNNIN TYEGGTHEAG  240
FKTGLTRVIN DYARKKGLIK ENDPNLSGDD VREGLTAIIS IKHPDPQFEG QTKTKLGNSE  300
ARTITDTLFS AALETFMLEN PDAAKKIVDK GLMAARARMA AKKARELTRR KSALEISNLP  360
GKLADCSSKD PSISELYIVE GDSAGGSAKQ GRDRHFQAIL PLRGKILNVE KARLDKILSN  420
NEVRSMITAL GTGIGEDFNL GKARYHKVVI MTDADVDGAH IRTLLLTFFY RYMRQIIENG  480
YVYIAQPPLY KVQQGKRVEY AYNDKELDDL LKTLPQTPKP GLQRYKGLGE MNATQLWETT  540
MDPSSRTLLQ VTLEDAMDAD ETFEML                                     566
```